United States Patent
Gupta et al.

(10) Patent No.: US 11,089,988 B2
(45) Date of Patent: *Aug. 17, 2021

(54) NON-INVASIVE METHOD AND SYSTEM FOR ESTIMATING ARTERIAL FLOW CHARACTERISTICS

(71) Applicant: Analytics For Life Inc., Toronto (CA)

(72) Inventors: Sunny Gupta, Belleville (CA); Shyamlal Ramchandani, Kingston (CA); Timothy William Fawcett Burton, Toronto (CA); William Sanders, Bethseda, MD (US); Ian Shadforth, Morrisville, NC (US)

(73) Assignee: Analytics for Life Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/524,475

(22) Filed: Jul. 29, 2019

(65) Prior Publication Data

US 2020/0054232 A1 Feb. 20, 2020

Related U.S. Application Data

(63) Continuation of application No. 15/633,330, filed on Jun. 26, 2017, now Pat. No. 10,362,950.
(Continued)

(51) Int. Cl.
*A61B 5/316* (2021.01)
*A61B 5/00* (2006.01)
(Continued)

(52) U.S. Cl.
CPC .............. *A61B 5/316* (2021.01); *A61B 5/026* (2013.01); *A61B 5/02007* (2013.01);
(Continued)

(58) Field of Classification Search
CPC .. A61B 5/04017; A61B 5/026; A61B 5/04085
See application file for complete search history.

(56) References Cited

U.S. PATENT DOCUMENTS 5,020,540 A 6/1991 Chamoun
5,029,082 A 7/1991 Shen et al.
(Continued)

FOREIGN PATENT DOCUMENTS

JP H09-131329 5/1997
JP 2007-510493 4/2007
(Continued)

OTHER PUBLICATIONS

Asadi, et al., "Cardiac Arrhythmia Recognition with Robust Discrete Wavelet-Based and Geometrical Feature Extraction via Classifiers of SVM and MLP-BP and PNN Neural Networks," Computing in Cardiology, Issue 43, (abstract, Figure 1), 2015, pp. 933-936.
(Continued)

*Primary Examiner* — Joseph M Dietrich
(74) *Attorney, Agent, or Firm* — Meunier Carlin & Curfman LLC

(57) ABSTRACT

The present disclosure facilitates the evaluation of wideband phase gradient information of the heart tissue to assess, e.g., the presence of heart ischemic heart disease. Notably, the present disclosure provides an improved and efficient method to identify and risk stratify coronary stenosis of the heart using a high resolution and wide-band cardiac gradient obtained from the patient. The patient data are derived from the cardiac gradient waveforms across one or more leads, in some embodiments, resulting in high-dimensional data and long cardiac gradient records that exhibit complex nonlinear variability. Space-time analysis, via numeric wavelet operators, is used to study the morphology of the cardiac gradient
(Continued)

data as a phase space dataset by extracting dynamical and geometrical properties from the phase space dataset.

40 Claims, 15 Drawing Sheets

Related U.S. Application Data

(60) Provisional application No. 62/354,673, filed on Jun. 24, 2016, provisional application No. 62/409,176, filed on Oct. 17, 2016.

(51) Int. Cl.
*A61B 5/02* (2006.01)
*A61B 5/282* (2021.01)
*A61B 5/026* (2006.01)
*A61B 5/1455* (2006.01)

(52) U.S. Cl.
CPC .............. *A61B 5/282* (2021.01); *A61B 5/726* (2013.01); *A61B 5/0006* (2013.01); *A61B 5/14551* (2013.01)

(56) References Cited

U.S. PATENT DOCUMENTS

| | | |
|---|---|---|
| 5,243,993 A | 9/1993 | Alexander et al. |
| 5,690,118 A | 11/1997 | Sornmo et al. |
| 5,823,957 A | 10/1998 | Faupel et al. |
| 5,954,660 A | 9/1999 | Legay et al. |
| 5,977,974 A | 11/1999 | Hatori et al. |
| 6,014,582 A | 1/2000 | He |
| 6,549,219 B2 | 4/2003 | Selker |
| 6,709,399 B1 | 3/2004 | Shen et al. |
| 7,992,102 B1 | 8/2011 | De Angelo |
| 8,521,266 B2 | 8/2013 | Narayan et al. |
| 8,707,211 B2 | 4/2014 | Yasui et al. |
| 8,790,255 B2 | 7/2014 | Behar |
| 8,923,958 B2 | 12/2014 | Gupta et al. |
| 9,035,888 B1 | 5/2015 | DeLatorre |
| 9,131,864 B2 | 9/2015 | Korenberg |
| 9,289,150 B1 | 3/2016 | Gupta et al. |
| D757,780 S | 5/2016 | Moriya |
| 9,408,543 B1 | 8/2016 | Gupta et al. |
| 9,597,021 B1 | 3/2017 | Gupta et al. |
| 9,737,229 B1 | 8/2017 | Gupta et al. |
| D844,013 S | 3/2019 | Peeters et al. |
| D857,046 S | 8/2019 | Huang et al. |
| 2002/0029068 A1 | 3/2002 | Lyster et al. |
| 2002/0156385 A1 | 10/2002 | Feng et al. |
| 2003/0105403 A1 | 6/2003 | Istvan et al. |
| 2006/0173364 A1 | 8/2006 | Clancy et al. |
| 2008/0118121 A1 | 5/2008 | Skinner et al. |
| 2008/0275353 A1 | 11/2008 | Bartal et al. |
| 2009/0167706 A1 | 7/2009 | Tan et al. |
| 2012/0063663 A1 | 3/2012 | Kawasaki |
| 2013/0023781 A1 | 1/2013 | Freeman et al. |
| 2013/0303871 A1 | 11/2013 | Brest Van Kempen et al. |
| 2014/0023255 A1 | 1/2014 | Lim et al. |
| 2014/0058844 A1 | 2/2014 | Jadeja et al. |
| 2014/0133803 A1 | 5/2014 | Rosenberg et al. |
| 2014/0194758 A1 | 7/2014 | Korenberg |
| 2014/0375298 A1 | 12/2014 | Garcia et al. |
| 2015/0133803 A1 | 5/2015 | Gupta et al. |
| 2015/0173707 A1 | 6/2015 | Ohuchi et al. |
| 2015/0216426 A1 | 8/2015 | Burton et al. |
| 2015/0272464 A1 | 10/2015 | Armoundas |
| 2015/0331995 A1 | 11/2015 | Zhao et al. |
| 2015/0342537 A1 | 12/2015 | Taylor et al. |
| 2016/0140707 A1 | 5/2016 | Abe et al. |
| 2016/0157802 A1 | 6/2016 | Anderson |
| 2016/0183822 A1 | 6/2016 | Gupta et al. |
| 2016/0249885 A1 | 9/2016 | Schneider et al. |
| 2016/0378936 A1 | 12/2016 | Burton et al. |
| 2017/0119272 A1 | 5/2017 | Gupta et al. |
| 2017/0209059 A1 | 7/2017 | Nabutovsky et al. |
| 2018/0060524 A1 | 3/2018 | Krimsky |
| 2018/0078146 A1 | 3/2018 | Shadforth et al. |

FOREIGN PATENT DOCUMENTS

| | | |
|---|---|---|
| JP | 2008-284352 | 11/2008 |
| JP | 2015-119768 | 7/2015 |
| JP | 2015-119786 | 7/2015 |
| JP | 2015-164560 | 9/2015 |
| WO | 2005/046471 | 5/2005 |
| WO | 2010/061335 | 6/2010 |
| WO | 2012/021307 | 2/2012 |
| WO | 2012/139116 | 10/2012 |
| WO | 2017/033164 | 3/2017 |

OTHER PUBLICATIONS

Edelsbrunner, H., et al., "Three-Dimensional Alpha Shapes," ACM Transactions on Graphics, vol. 13, No. 1, 1994, pp. 43-72.

Freund, Y., et al., "A decision-theoretic generalization of on-line learning and an application to boosting," Proceedings of the Second European Conference on Computational Learning Theory, 1995, 15 pages.

Itu, et al., "A machine-learning approach for computation of fractional flow reserve from coronary computed tomography," Journal of Applied Physiology, vol. 121, Issue 1, Apr. 14, 2016, pp. 42-52.

Jaarsma, et al., "Diagnostic performance of noninvasive myocardial perfusion imaging using single-photon emission computed tomography, cardiac magnetic resonance, and positron emission tomography imaging for the detection of obstructive coronary artery disease: a meta-analysis," Journal of the American College of Cardiology, vol. 59, Issue 19, 2012, pp. 1719-1728.

Jobbagy, "Biomedical Instrumentation," Typotex Kiado, Budapest University of Technology and Economics, Mar. 31, 2015, pp. 1-241.

Khan, et al., "Wavelet Based ECG Denoising Using Signal-Noise Residue Method," $5^{th}$ International Conference on Bioinformatics and Biomedical Engineering (abstract, section III, Figure 1), May 2011, 4 pages.

Koszegi, Z., et al., "Holistic polar map for integrated evaluation of cardiac imaging results," Computerized Medical Imaging and Graphics, vol. 31, 2007, pp. 577-586.

Lorenz, E., "Deterministic Nonperiodic Flow," Journal of the Atmospheric Sciences 1963, vol. 20, No. 2, pp. 130-141.

Mallat, S.G., et al., "Matching Pursuits with Time-Frequency Dictionaries," IEEE Transactions on Signal Processing, vol. 41, No. 12, 1993, pp. 3397-2415.

McKee, J., et al., "Sigma-Delta Analogue-to-Digital Converters for ECG Signal Acquisition," Proceedings of $18^{th}$ Annual International Conference of the IEEE Engineering in Medicine and Biology Society, Amsterdam, Netherlands, Oct. 31, 1996-Nov. 3, 1996, pp. 19-20.

Walmsley, J., et al., "Fast Simulation of Mechanical Heterogeneity in the Electrically Asynchronous Heart Using the MultiPatch Module," Plos Computational Biology, retrieved on Nov. 14, 2019 at https://journals.plos.org/ploscompbiol/article?id=10.1371/journal.pcbi.1004284, 2015, 2 pages.

Supplementary Search Report, dated Nov. 22, 2019, received in connection with corresponding EP Patent Application No. 17814879.7.

International Search Report and Written Opinion, dated Dec. 14, 2017, received in connection with International Patent Application No. PCT/IB2017/055748.

International Search Report and Written Opinion, dated Dec. 14, 2017, received in connection with International Patent Application No. PCT/IB2017/055125.

International Search Report, dated Oct. 24, 2017, received in connection with International Patent Application No. PCT/IB2017/053814.

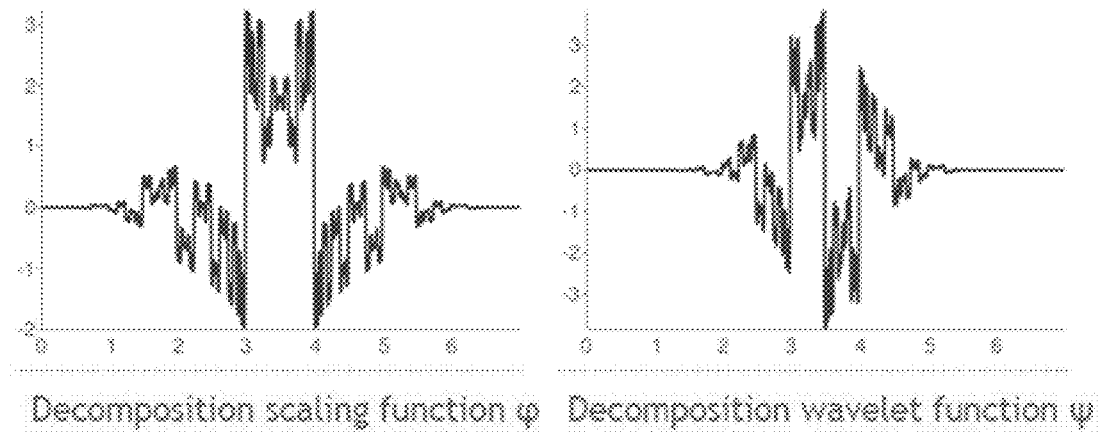
FIG. 10A  FIG. 10B
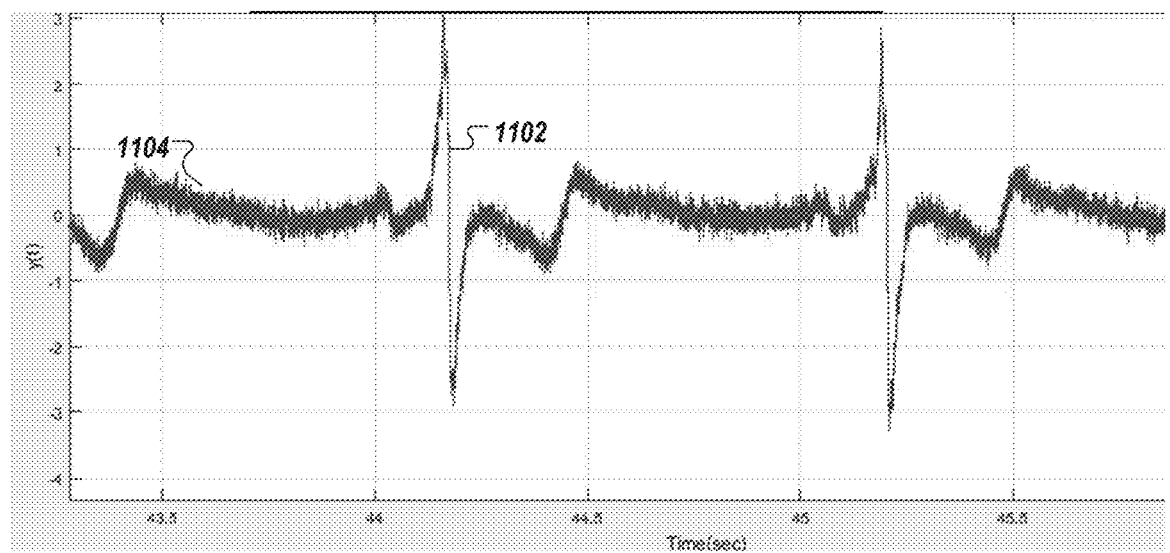
FIG. 11

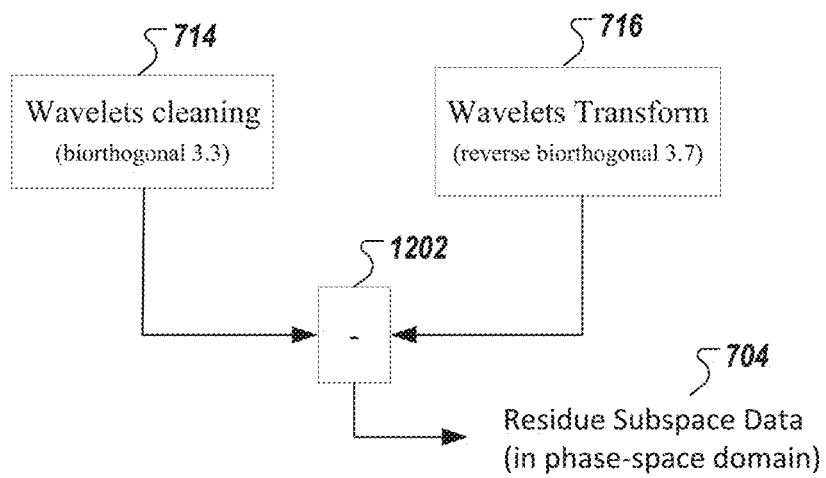
FIG. 12
Wavelet Reverse Biorthogonal 3.7 (bior3.7)
Wavelet and scaling functions
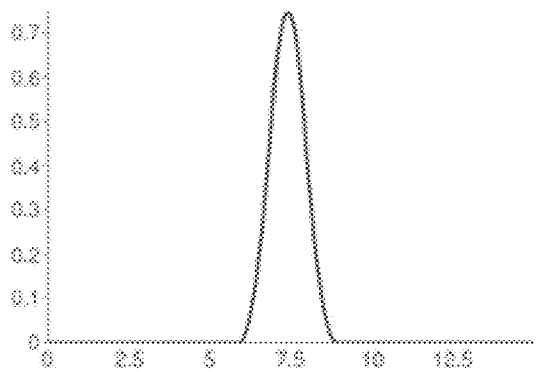
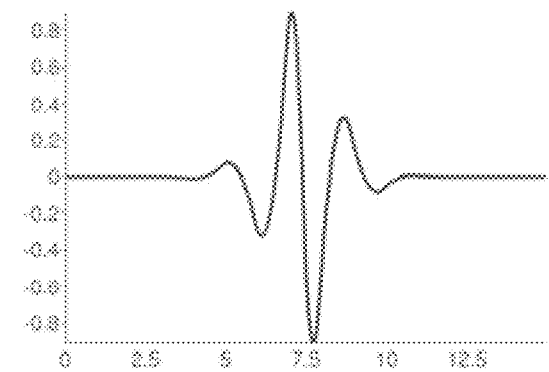
FIG. 13A  FIG. 13B

| cADLAD Stage 1 | |
|---|---|
| Number of subjects reported on: | 523 |
| Number of subjects for ML training: | 429 |
| Number of subjects in verification population: | 94 |
| ROC curve: | 0.80 |
| cPSTA PPV: | 47% |
| cPSTA NPV: | 86% |

Predictor A

| cPSTA Diagnosis | | Angiography Results | |
|---|---|---|---|
| | | Significant CAD | Non/non significant CAD |
| | CAD+ | TP: 23 | FP: 26 |
| | CAD- | FN: 2 | TN: 43 |

FIG. 21

| cADLAD Stage 1 | |
|---|---|
| Number of subjects reported on: | 523 |
| Number of subjects for ML training: | 429 |
| Number of subjects in verification population: | 94 |
| ROC curve: | 0.78 |
| cPSTA PPV: | 49% |
| cPSTA NPV: | 82% |

Predictor B

| cPSTA Diagnosis | | Angiography Results | |
|---|---|---|---|
| | | Significant CAD | Non/non significant CAD |
| | CAD+ | TP: 21 | FP: 22 |
| | CAD- | FN: 4 | TN: 47 |

FIG. 22

NON-INVASIVE METHOD AND SYSTEM FOR ESTIMATING ARTERIAL FLOW CHARACTERISTICS

RELATED APPLICATIONS

This is a continuation application of U.S. patent application Ser. No. 15/633,330, filed Jun. 26, 2017, now U.S. Pat. No. 10,362,950, which claims priority to, and the benefit of, U.S. Provisional Application No. 62/354,673, filed Jun. 24, 2016, and U.S. Provisional Application No. 62/409,176, filed Oct. 17, 2016, each of which is incorporated by reference herein in its entirety.

FIELD OF THE INVENTION

The present disclosure generally relates to non-invasive methods and systems for characterizing cardiovascular circulation. More specifically, the present disclosure relates to non-invasive methods that utilize unfiltered wide-band cardiac phase gradient data to generate residue subspace and noise subspace data, for example, to be used in the prediction and localization of coronary artery stenoses, localizing and/or estimating fractional flow reserve, and characterizing myocardial ischemia.

BACKGROUND

Vascular diseases are often manifested by reduced blood flow due to atherosclerotic occlusion of vessels. For example, occlusion of the coronary arteries supplying blood to the heart muscle is a major cause of heart disease. Invasive procedures for relieving arterial blockage such as bypass surgery and stent placement with a catheter rely on estimates of occlusion characteristics and blood flow through the occluded artery. These estimates are based on measurements of occlusion size and/or blood flow. Unfortunately, current methods of occlusion size and blood flow measurement require invasive procedures such as coronary angiography, which requires cardiac catheterization. This procedure involves a long, thin, flexible catheter being placed into a blood vessel in the arm, groin (upper thigh), or neck; the catheter is then threaded to the heart. Through the catheter, a physician can perform a visual evaluation of the inner diameter of a vessel with cineangiography or fluoroscopy and/or use a small sensor on the tip of the wire (commonly a transducer) to measure parameters such as pressure, temperature, and flow to determine the severity of the lesion; and fractional flow reserve (FFR). These minimally invasive diagnostic tests on the heart carry the risk of stroke, heart attack, injury to the catheterized artery/heart, irregular heart rhythms, kidney damage, infection, and radiation exposure from X-rays. These procedures are time consuming, require expertise in the interpretation of the results and are expensive.

Stenosis geometry is also important in the therapeutic phase when balloon angioplasty, stenting or drug delivery procedures are subsequently performed. For example, precise stent placement is critical for reducing the risk of restenosis. Thus, decisions on whether or not to use any of the blockage relieving methods and which of the methods should be used are often based on partial information and do not take into account coronary collateralization. The ischemic stress often induces the increase in collateral circulation in coronary small vessel which at times will compensate for distal vessel blockage. Further, the evaluation of therapeutic success is also problematic, where both occlusion opening and stent position have to be evaluated. One class of methods, predominantly used today, require a lengthy procedure to find and determine severity, blockage to blood flow, of the lesion or lesions. Contemporary techniques evaluate the cardiac gradient phase-space changes and correlate the changes with cardiac computed tomography (CT), myocardial perfusion imaging, and cardiac angiography. The surface cardiac gradient contains detailed information on the electrophysiology of the chambers recorded. Because surface cardiac gradient represents the summation of the individual action potentials from each and every cardiac cell in syncytium, in theory, any information that might be determined from measurement of the orchestrated cellular action potential should be available on a "global" level in the surface. Moreover, although information relating to the influence of myocardial tissue architecture on conduction properties is inherent in the surface cardiac gradient, the challenge is in the discrimination of the pertinent information from these long quasi-periodic cardiac gradient signals while excluding noise contamination. Still further, there is a distinct lack of non-invasive tools available to enhance identification of high-risk patients and thus to trial preventive strategies in a non-invasive manner.

SUMMARY

The present disclosure facilitates the evaluation of wideband phase gradient information of heart tissue to assess the presence of heart ischemic heart disease. Notably, the present disclosure provides an improved and efficient method to identify and risk-stratify coronary stenosis of the heart using a high resolution and wide-band cardiac gradient obtained from the patient or subject. The patient data are derived from the cardiac gradient waveforms across multiple leads, in some embodiments, resulting in high-dimensional data and long cardiac gradient records that exhibit complex nonlinear variability. Space-time analysis, via numeric wavelet operators, is used to study the morphology of the cardiac gradient data as a phase space dataset by extracting dynamical and geometrical properties from the phase space dataset. The numeric wavelet operators facilitate real-time, or near real-time processing of the collected wide-band cardiac gradient dataset to generate a residue subspace dataset and a noise subspace dataset. The residue subspace dataset and noise subspace dataset, in some embodiments, are generated as multi-dimensional datasets (e.g., three-dimensional) and are well-suited to image and graphics processing. The extracted morphology of the residue subspace dataset and noise subspace dataset are fed, as parameters and variables, to a learning algorithm to associate them with abnormalities of the heart understudy.

As such, the present disclosure provides for a non-invasive system and method whereby cardiac gradient measurements can be taken and transformed to locate and visualize, via rendered images, architectural features of the myocardium and to characterize abnormalities in the heart and the cardiovascular function. Furthermore, the present disclosure provides a system and method to visualize (e.g., an inverse cardiac gradient problem) architectural features of the heart and the location of abnormally conducting/functioning cardiac tissue. Furthermore, the present disclosure provides a system and method to output, as parameters, to therapy, a treatment device, or a diagnostic device, architectural features of the heart and the location of abnormally conducting/functioning cardiac tissue.

In an aspect, a method or methods are disclosed of non-invasively identifying and/or measuring myocardial ischemia, identifying one or more stenoses, and/or localizing and/or estimating fractional flow reserve in a mammalian subject or patient. The method(s) include(s) obtaining a plurality of wide-band gradient signals simultaneously from the subject via at least one of electrode (e.g. one or more surface electrodes, non-contact electrodes or other types of biopotential sensing apparatus) and determining, via one or more processors, one or more coronary physiological parameters of the subject selected from the group consisting of a fractional flow reserve estimation, a stenosis value, and a myocardial ischemia estimation (e.g., and/or other arterial flow characteristics), based on a residue subspace dataset and a noise subspace dataset derived from data associated with the plurality of wide-band gradient signals.

In some embodiments, the residue subspace dataset is determined by generating a first wavelet signal dataset by performing a first wavelet operation (via, e.g., a first phase linear wavelet operator) on data derived from the plurality of wide-band gradient signals; generating a second wavelet signal dataset by performing a second wavelet operation (via, e.g., a second phase linear wavelet operator) on the first wavelet signal data; and subtracting values of the first wavelet signal dataset from values of the second wavelet signal dataset to generate the residue subspace dataset, wherein the residue subspace dataset comprises a three-dimensional phase space dataset in a space-time domain.

In some embodiments, the method or methods further include(s) extracting a first set of morphologic features of the three-dimensional phase space dataset, wherein the first set of extracted morphologic features include parameters selected from the group consisting of a three-dimensional (3D) volume value, a void volume value, a surface area value, a principal curvature direction value, and a Betti number value.

In some embodiments, the first set of extracted morphologic features is extracted using an alpha-hull operator.

In some embodiments, the method or methods further include(s) dividing the three-dimensional phase space dataset into a plurality of segments, each comprising non-overlapping portions of the three-dimensional phase space data set and extracting a second set of morphologic features of each of the plurality of segments, wherein the second set of extracted morphologic features includes parameters selected from the group consisting of a 3D volume value, a void volume value, a surface area value, a principal curvature direction value, and a Betti number value.

In some embodiments, the second set of extracted morphologic features is extracted using an alpha-hull operator.

In some embodiments, the plurality of segments comprises a number of segments selected from the group consisting of 3, 4, 5, 6, 7, 8, 9, 10, 11, 12, 13, 14, 15, 16, 17, 18, 19, and 20.

In some embodiments, the noise subspace dataset is determined by generating a first wavelet signal dataset by performing a first wavelet operation (e.g., a first phase linear wavelet operator) on data derived from the plurality of wide-band gradient signals and generating a second wavelet signal dataset by performing a second wavelet operation (e.g., a second phase linear wavelet operator) on the first wavelet signal data, the second wavelet signal data comprising the noise subspace dataset, wherein the noise subspace dataset comprises a 3D phase space dataset in a space-time domain.

In some embodiments, the method or methods further include(s) extracting a set of morphologic features of the 3D phase space data set, wherein the set of extracted morphologic features includes parameters selected from the group consisting of a 3D volume value, a void volume value, a surface area value, a principal curvature direction value, and a Betti number value.

In some embodiments, the set of extracted morphologic features is extracted using an alpha-hull operator.

In some embodiments, the method or methods further include(s) dividing the three-dimensional phase space data set into a plurality of segments, each comprising non-overlapping portion of the three-dimensional phase space dataset and extracting a second set of morphologic features of each of the second plurality of segments, wherein the second set of extracted morphologic features includes parameters selected from the group consisting of a 3D volume value, a void volume value, a surface area value, a principal curvature direction value, and a Betti number value.

In some embodiments, the second set of extracted morphologic features is extracted using an alpha-hull operator.

In some embodiments, the second of segments comprises a number of segments selected from the group consisting of 3, 4, 5, 6, 7, 8, 9, 10, 11, 12, 13, 14, 15, 16, 17, 18, 19, and 20.

In some embodiments, the residue subspace dataset is associated with a first shape of a first noise geometry and the noise subspace dataset is associated with a second shape of a second noise geometry corresponding to stochastic noise.

In some embodiments, the plurality of wide-band gradient signals are simultaneously obtained having a lag or skew of less than about 10-femtoseconds between each of the signals.

In some embodiments, each of the plurality of wide-band gradient signals is unfiltered prior to, and during, the processing, to generate the residue subspace dataset and the noise subspace dataset.

In some embodiments, each of the plurality of wide-band gradient signals comprises cardiac data in a frequency domain having frequency components greater than about 1 kHz.

In some embodiments, each of the plurality of wide-band gradient signals comprises cardiac frequency information at a frequency selected from the group consisting of about 1 kHz, about 2 kHz, about 3 kHz, about 4 kHz, about 5 kHz, about 6 kHz, about 7 kHz, about 8 kHz, about 9 kHz, and about 10 kHz.

In some embodiments, each of the plurality of wide-band gradient signals comprises cardiac frequency information at a frequency between about 0 Hz and about 50 kHz.

In some embodiments, each of the plurality of wide-band gradient signals comprises cardiac frequency information at a frequency between about 0 Hz and about 500 kHz.

In some embodiments, the method or methods further include(s) associating, via a first machine learning operation (e.g., neural nets, formula learning, etc.), the extracted first set of morphologic features to a plurality of candidate models associated with estimation of the fractional flow reserve estimation, the stenosis value, and the myocardial ischemia estimation; and selecting a candidate model of the plurality of candidate models to determine an output of each of the estimation of the fractional flow reserve estimation, the stenosis value, and the myocardial ischemia estimation.

In some embodiments, the method or methods further include(s) visualizing the determined one or more coronary physiological parameters.

In some embodiments, the fractional flow reserve estimation, the stenosis value, and the myocardial ischemia estimation are presented at one or more corresponding coronary regions on an image of a heart (e.g., via a standardized 17-segment model of the heart).

In some embodiments, the method or methods further include(s) outputting, to a surgical device or a diagnostic device, the determined one or more coronary physiological parameters.

In some embodiments, one of more of the at least one electrode are selected from the group consisting of surface electrodes, intracardiac electrodes, and non-contact electrodes.

In some embodiments, the methods include(s) identifying one or more significant artery stenoses, the identification having an AUC-ROC score ("area-under-the-curve" and "receiver operating characteristic" score) greater than about 0.7 in a verification phase.

In another aspect, a system is disclosed, e.g., of non-invasively identifying and/or measuring myocardial ischemia, identifying one or more stenoses, and/or localizing and/or estimating fractional flow reserve, e.g., via a wide-band biopotential measuring apparatus. The system includes a processor and a memory having instructions stored thereon, wherein execution of the instructions causes the processor to obtain a plurality of wide-band gradient signals simultaneously from one or more electrodes (e.g., surface electrodes, non-contact electrodes or other types of biopotential sensing apparatus) and determine one or more coronary physiological parameters selected from the group consisting of a fractional flow reserve estimation, a stenosis value, and a myocardial ischemia estimation, based on a residue subspace dataset and a noise subspace dataset derived from data associated with the plurality of wide-band gradient signals.

In some embodiments, execution of the instructions further causes the processor to cause visualization of the determined coronary physiological parameter to be presented on a display.

In some embodiments, the execution of the instructions further causes the processor to output, to a therapy device, the determined one or more coronary physiological parameters.

In another aspect, a computer readable medium is disclosed having instructions stored thereon, wherein execution of the instructions causes a processor to determine one or more coronary physiological parameters selected from the group consisting of a fractional flow reserve estimation, a stenosis value and a myocardial ischemia estimation, based on a residue subspace dataset and a noise subspace dataset derived from data associated with the plurality of wide-band gradient signals simultaneously obtained from at least one surface electrode.

In some embodiments, execution of the instructions further causes the processor to cause visualization of the determined coronary physiological parameter to be presented on a display.

In some embodiments, execution of the instructions causes the processor to output, to a therapy device, the determined one or more coronary physiological parameters.

BRIEF DESCRIPTION OF THE DRAWINGS

The components in the drawings are not necessarily to scale relative to each other and like reference numerals designate corresponding parts throughout the several views:

FIGS. 10A and 10B are diagrams of an example wavelet transformation used to generate the multi-dimensional wavelet cleansed dataset, in accordance with an illustrative embodiment.

FIG. 11 is a diagram of an example time series dataset of a wavelet cleansed dataset, in accordance with an illustrative embodiment.

FIG. 12 is a diagram of an example wavelet-based operation to generate the multi-dimensional residue subspace dataset, in accordance with an illustrative embodiment.

FIGS. 13A and 13B are diagrams of an example wavelet transformation used to generate the multi-dimensional wavelet cleansed dataset, in accordance with an illustrative embodiment.

FIG. 16 shows an example multi-dimensional residue subspace dataset of a subject without ischemia. FIG. 17 shows an example multi-dimensional residue subspace dataset of a subject with ischemia.

FIG. 18 shows an example multi-dimensional noise subspace dataset of a subject without ischemia. FIG. 19 shows an example multi-dimensional noise subspace dataset of a subject with ischemia.

FIGS. 21 and 22 are diagrams showing results of a study conducted using the analysis of FIG. 1, in accordance with an illustrative embodiment.

DETAILED DESCRIPTION

Figure 1:
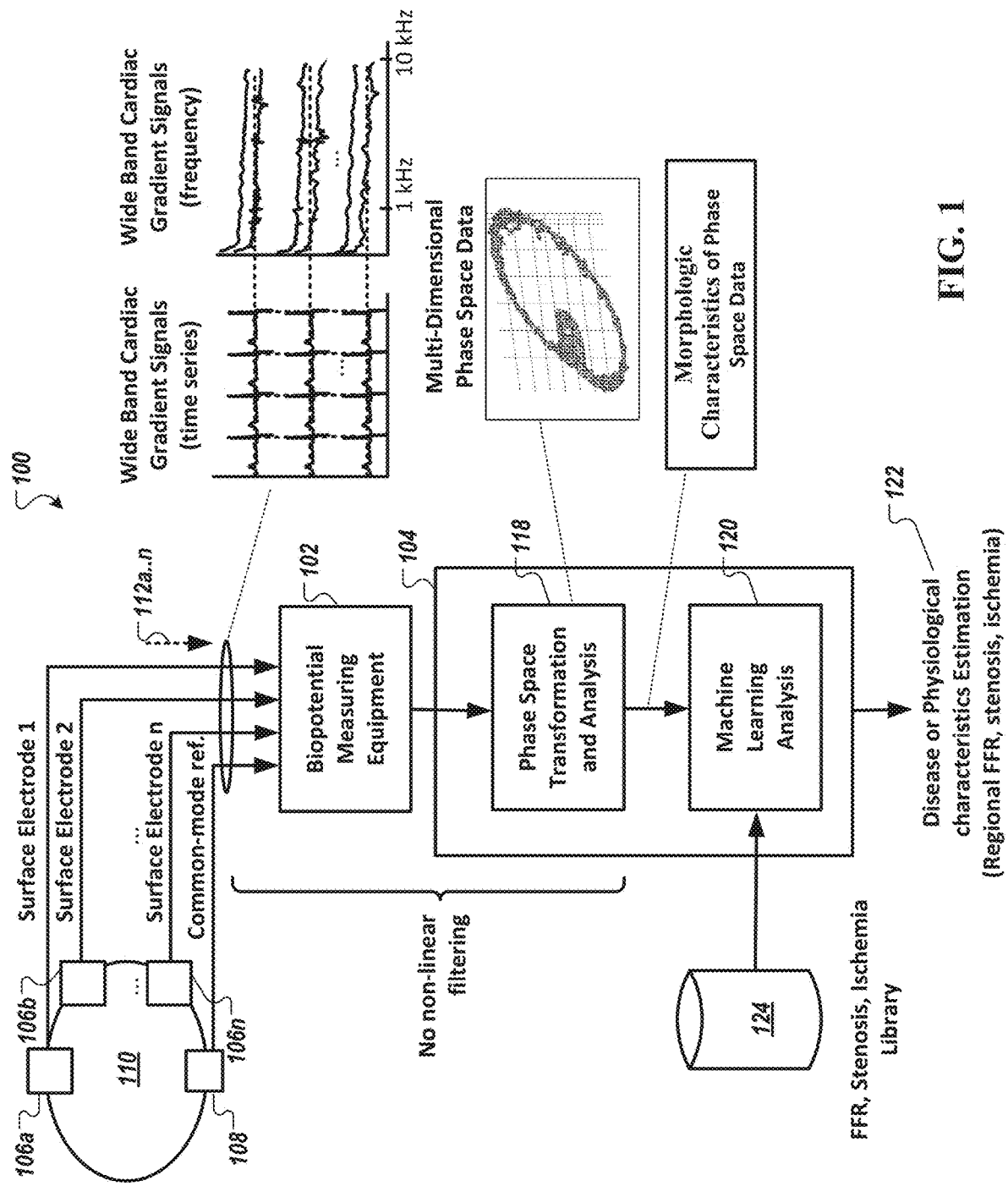
FIG. 1 is a diagram of a system for non-invasively determining arterial flow characteristics (e.g., presence of myocardial ischemia, stenosis identification, localization, and fractional flow reserve estimation) in the heart using wide-band cardiac gradient data, in accordance with an illustrative embodiment.

The components in the drawings are not necessarily to scale relative to each other and like reference numerals designate corresponding parts throughout the several views.

FIG. 1 is a diagram of a system for non-invasively determining arterial flow characteristics in the heart using wide-band cardiac gradient data, in accordance with an illustrative embodiment. As shown in FIG. 1, the system 100 includes a wide-band biopotential measuring equipment 102 and an analysis subsystem 104. The wide-band biopotential measuring equipment 102 collects wide-band biopotential signals 112 (shown as 112a . . . n) (also referred to herein as wide-band cardiac gradient signal data 112) from a subject or patient 110, via at least one electrode 106 (shown as surface electrodes 106a, 106b, 106n), and corresponding common-mode reference lead 108, all of which are in the system of FIG. 1 are attached to the surface of the mammalian subject or patient 110 (e.g., the skin of an animal or a person). The wide-band biopotential measuring equipment 102 may be any device configured to capture unfiltered electrophysiological signals such that the spectral component(s) of the signals are not altered. That is, all of the captured signal, if not a significant portion of the captured signal, includes components conventionally perceived or treated as being noise, e.g., those in the frequency range of greater than about 1 kHz. To this end, the wide-band biopotential measuring equipment 102 captures, converts, and analyzes the collected wide-band biopotential signals 112 without any filtering (via hardware circuitry, or digital signal processing) that affects phase linearity of the signal of the wide-band biopotential signals 112. That is, only phase deterministic operations, numeric or analytical, are performed in the phase space transformation and analysis. Phase distortions are non-deterministic distortions that cause shifts in the frequency component of a signal.

An example wide-band biopotential measuring equipment 102 is described in U.S. patent application Ser. No. 15/248, 838, published as US2017/0119272, titled "Method and Apparatus for Wide-Band Gradient Signal Acquisition," which is incorporated by reference herein in its entirety. In some embodiments, the wide-band biopotential measuring equipment 102 is configured to record unfiltered physiologic signals at a rate of about 8 kHz at a number of observation points on the patient or subject (in a resting position) for 210 seconds. The resultant signal recording is then securely transmitted to a cloud-based repository whereupon it is automatically queued for processing. In some embodiments, the resultant signal recording is securely transmitted to a cloud-based repository whereupon it is automatically queued for processing. The processing pipeline derives the phase energy of the thoracic system by taking the multi-dimensional (spatial temporal) transformation of the signals and subsequently reconstructs this into a phase space model of the patient's heart.

The inventors have discovered that wide-band biopotential signals, having energy and frequency components beyond those of conventional electrocardiography (ECG) and traditionally perceived or treated as random noise, includes measurable data of the heart physiology that can be discriminated by genetic algorithms (and other machine learning algorithms) to assess regional flow characteristics of the heart, including for example an estimated value for stenosis and the identification of ischemia and a fractional flow reserve (FFR) of specific arteries and branches thereof. Noise removal (e.g., by applying cleaning techniques to the data resulting in the same amount of data as prior to noise removal) is a fundamental step in signal processing. However, the exemplified method and system process the entire obtained biopotential signals without any noise removal operations. What has heretofore been perceived and/or classified as unwanted noise in the wide-band data is, in many cases, the signal of interest. Examples of noise removal that is not performed include, but are not limited to, analog-based low-pass filters, band-pass filters, high-pass filters as well as digital-based filters such as FIR filters, Butterworth filters, Chebyshev filters and median filters (among others) that are configured to change the phase linearity of the processed signals. It is noted that analog-based low-pass filters, band-pass filters, high-pass filters as well as digital-based filters, that are configured to be phase linear, may be used. In some embodiments, the signal may be processed via phase linear operations to allow for analysis of specific aspects of the high-frequency wide-band data.

As described in U.S. patent application Ser. No. 15/248, 838, in some embodiments, the wide-band biopotential measuring equipment 102 is configured to capture one or more biosignals, such as biopotential signals, in microvolt or sub-microvolt resolutions—resolutions that are at, or significantly below, the noise-floor of conventional electrocardiographic and biosignal acquisition instruments. In some embodiments, the wide-band biopotential measuring equipment 102 is configured to acquire and record wide-band phase gradient signals (e.g., wide-band cardiac phase gradient signals, wide-band cerebral phase gradient signals) that are simultaneously sampled, in some embodiments, having a temporal skew or "lag" of less than about 1 μs, and in other embodiments, having a temporal skew or lag of not more than about 10 femtoseconds. Notably, the exemplified system minimizes non-linear distortions (e.g., those that can be introduced via certain filters) in the acquired wide-band phase gradient signal so as to not affect the information therein.

Referring still to FIG. 1, the analysis system 104 is configured to generate a phase space map to be used in subsequent phase space analysis 118 later described herein. The output of the phase space analysis is then evaluated using machine learning analysis 120 to assess parameters 122 associated with a presence of a disease or physiological characteristic such as regional arterial flow characteristics. In some embodiments, the machine learning analysis 120 may use a library 124 of quantified FFR, stenosis, and ischemia data in the assessment of the obtained wide-band cardiac gradient signal data 112. The output 122 of a processor performing the analysis 104 is then transmitted to a graphical user interface, such as, e.g., a touchscreen or other monitor, for visualization. The graphical user interface, in some embodiments, is included in a display unit configured to display parameters 122. In some embodiments, the graphical user interface displays intermediate parameters such as a 3D phase space plot representation of the biopotential signal data and virtual biopotential signal data. In other embodiments, the output of the processor is then transmitted to one or more non-graphical user interfaces (e.g., printout, command-line or text-only user interface), directly to a database or memory device for, e.g., later retrieval and/or additional analysis, or combinations thereof.

As used herein, the term "processor" refers to a physical hardware device that executes encoded instructions for performing functions on inputs and creating outputs. The processor may include one or more processors, each configured to execute instructions and process data to perform one or more functions associated with a computer for indexing images. The processor may be communicatively coupled to RAM, ROM, storage, database, I/O devices, and interface. The processor may be configured to execute sequences of computer program instructions to perform various processes.

Example Wide-Band Cardiac Gradient Signal

Figure 3:
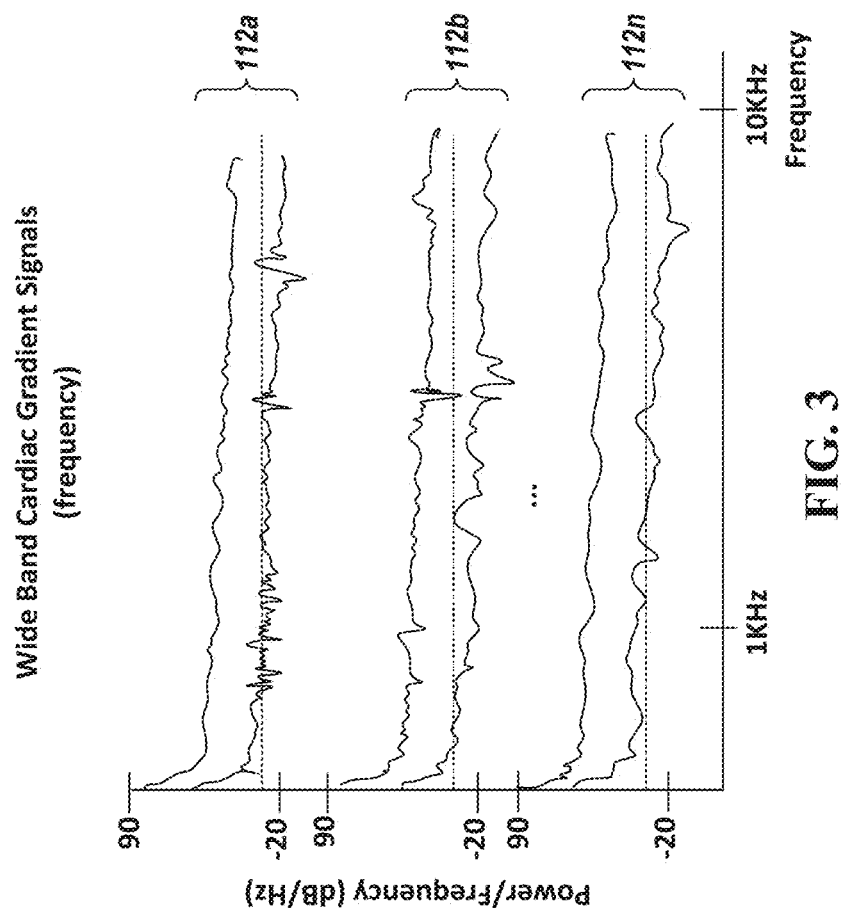
FIG. 3 is a diagram of an example wide-band cardiac gradient signal shown in the frequency domain, in accordance with an illustrative embodiment.
Figure 2:
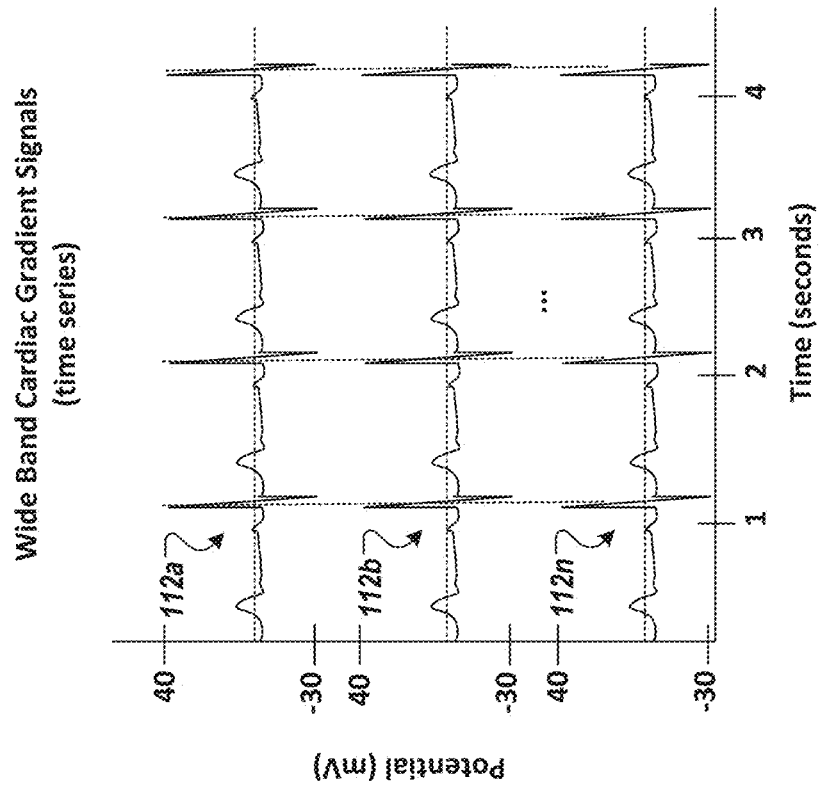
FIG. 2 is a diagram of an example wide-band cardiac gradient signal shown as a time series data, in accordance with an illustrative embodiment.

FIG. 2 (reproduced in FIG. 1) is a diagram of an example wide-band cardiac gradient signal 112 shown as time series data, in accordance with an embodiment. FIG. 3 (reproduced also in FIG. 1) is a diagram of the example wide-band cardiac gradient signal 112 of FIG. 2 shown in the frequency domain, in accordance with an embodiment. As shown in FIG. 3, the wide-band cardiac gradient signal 112 has a frequency component greater than 1 kHz, which is significantly higher than conventional electrocardiogram measurements. In some embodiments, the wide-band cardiac gradient signal 112 has a frequency component up to about 4 kHz (e.g., about 0 Hz to about 4 kHz). In some embodiments, the wide-band cardiac gradient signal 112 has a frequency component up to about 5 kHz (e.g., about 0 Hz to about 5 kHz). In some embodiments, the wide-band cardiac gradient signal 112 has a frequency component up to about 6 kHz (e.g., about 0 Hz to about 6 kHz). In some embodiments, the wide-band cardiac gradient signal 112 has a frequency component up to about 7 kHz (e.g., about 0 Hz to about 7 kHz). In some embodiments, the wide-band cardiac gradient signal 112 has a frequency component up to about 8 kHz (e.g., about 0 Hz to about 8 kHz). In some embodiments, the wide-band cardiac gradient signal 112 has a frequency component up to about 9 kHz (e.g., about 0 Hz to about 9 kHz). In some embodiments, the wide-band cardiac gradient signal 112 has a frequency component up to about 10 kHz (e.g., about 0 Hz to about 10 kHz). In some embodiments the wide-band cardiac gradient signal 112 has a frequency component up to 50 kHz (e.g., about 0 Hz to about 50 kHz).

Figure 4:
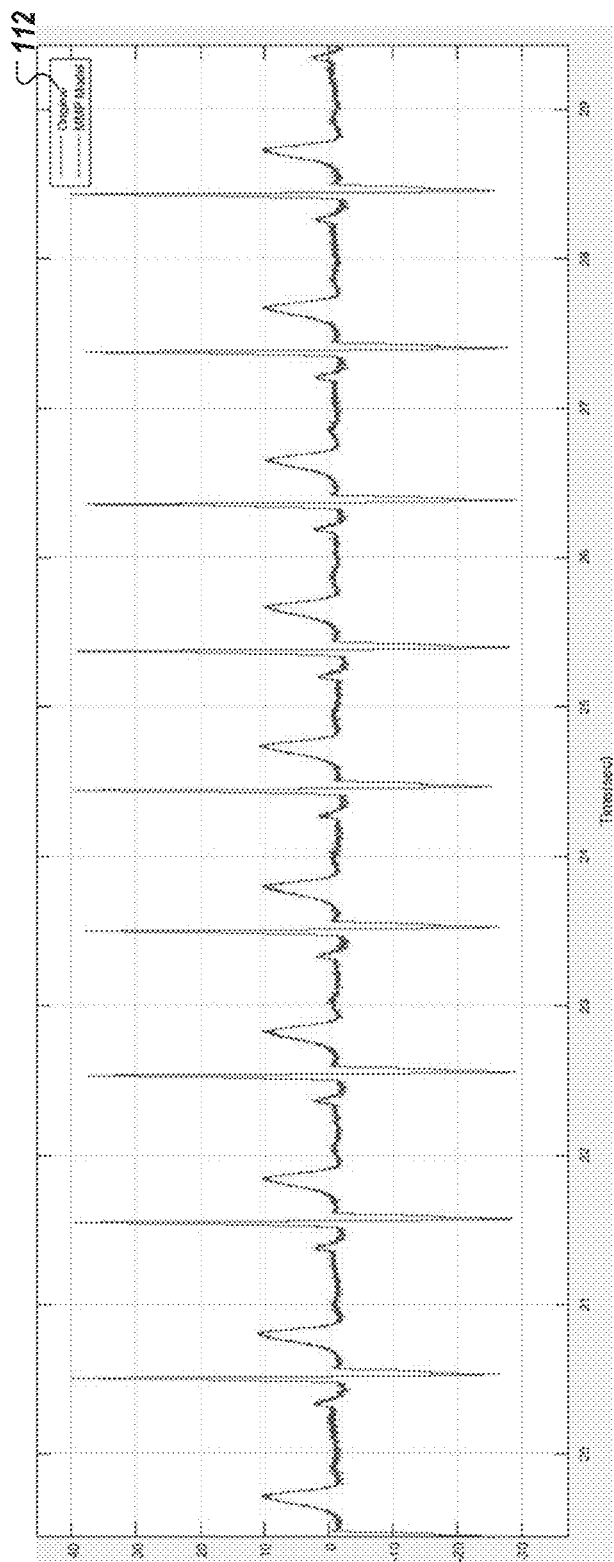
FIG. 4 is a time-series plot of an example wide-band cardiac gradient signal associated with a single surface electrode, in accordance with an illustrative embodiment.

FIG. 4 is a time-series plot of an example wide-band cardiac gradient signal 112 associated with a single surface electrode, in accordance with an embodiment. The plot shows the signal in mV over time (in seconds)

Figure 5:
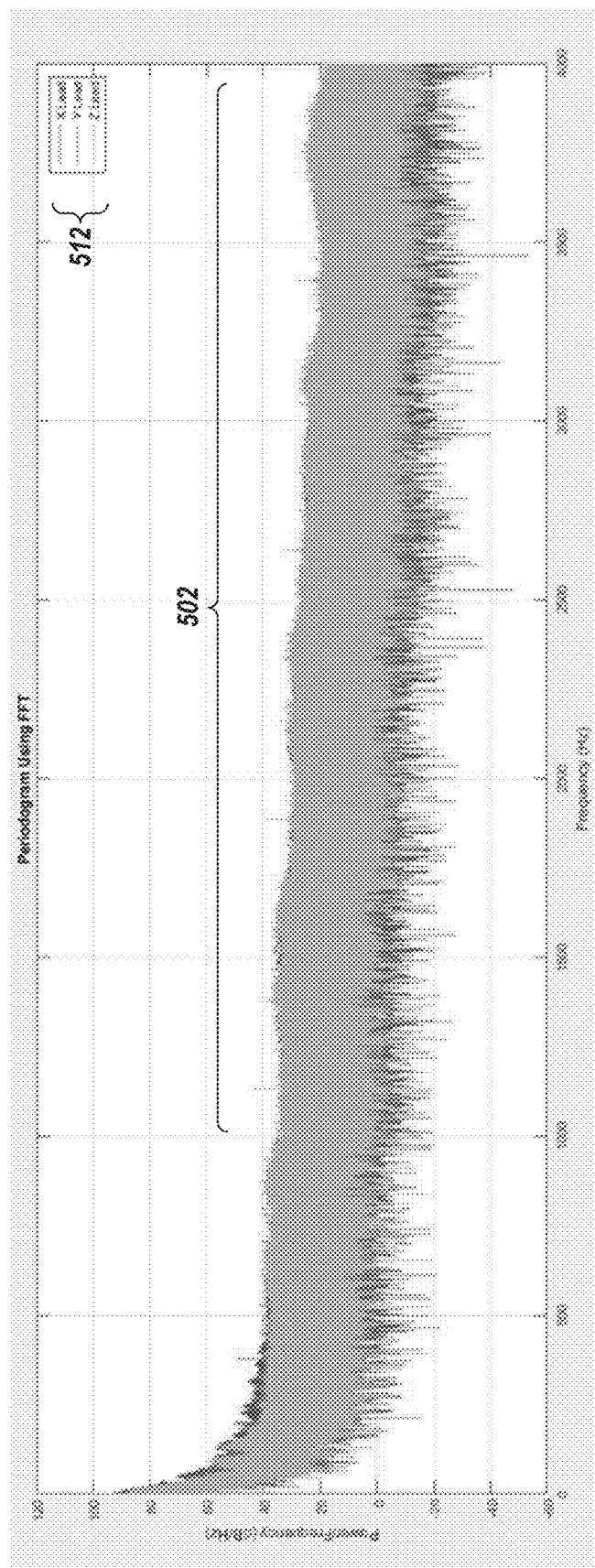
FIG. 5 is a frequency plot of an example wide-band cardiac gradient signal associated with three surface electrodes, in accordance with an illustrative embodiment.

FIG. 5 is a frequency plot of an example wide-band cardiac gradient signal 112 associated with three surface electrodes, in accordance with an embodiment. As shown, FIG. 5 includes frequency components of the wide-band cardiac gradient signal 112 up to 4 kHz. As further shown, the presented wide-band cardiac gradient signal 112 has power, in the frequency domain, between −20 dB and 20 dB at frequencies greater than 1 kHz. This portion 502 of the wide-band cardiac gradient signal 112 includes topologic and functional information about the cardiac tissue and its underlying structure that can be used to determine regional flow characteristics such as estimation of regional FFR, estimation of region stenosis, and identification and/or estimation of a degree of regional ischemia.

Wide-band cardiac gradient signals (e.g., having frequencies between about 1 kHz and about 10 kHz) facilitate phase space analysis on unevenly sampled data. In some embodiments, the wide-band cardiac gradient signals have higher sampling rates during intervals of interest and lower sampling rates during other intervals to facilitate minimization of the resulting data set size. This varying sampling rate may be used in application where data storage is limited. Many non-linear functions (e.g., such as those used in phase space analysis) operate more effectively at identifying amplitudes with points that are unevenly spaced in the time domain. The much higher sampling rate as compared to those of the highest frequencies of interest (e.g., 10 times greater than those of the highest frequencies of interest) facilitates a correctly characterized shape of the signal system. This is similar to Lorenz systems, where very high frequencies are beneficial to correctly model the shape of the system in phase space. Example of the Lorenz system is described in Lorenz, Edward Norton, "Deterministic non-periodic flow", Journal of the Atmospheric Sciences 20 (2), pages 130-141 (1963), the entirety of which is hereby incorporated by reference.

Example Ultra-Wide-Band Cardiac Gradient Signal

In some embodiments, the exemplified method and system are used to classify ultra-wide-band cardiac gradient signals having negative spectral energy signatures as high as about 500 kHz (e.g., having frequencies between about 1 kHz and about 500 kHz).

Figure 6:
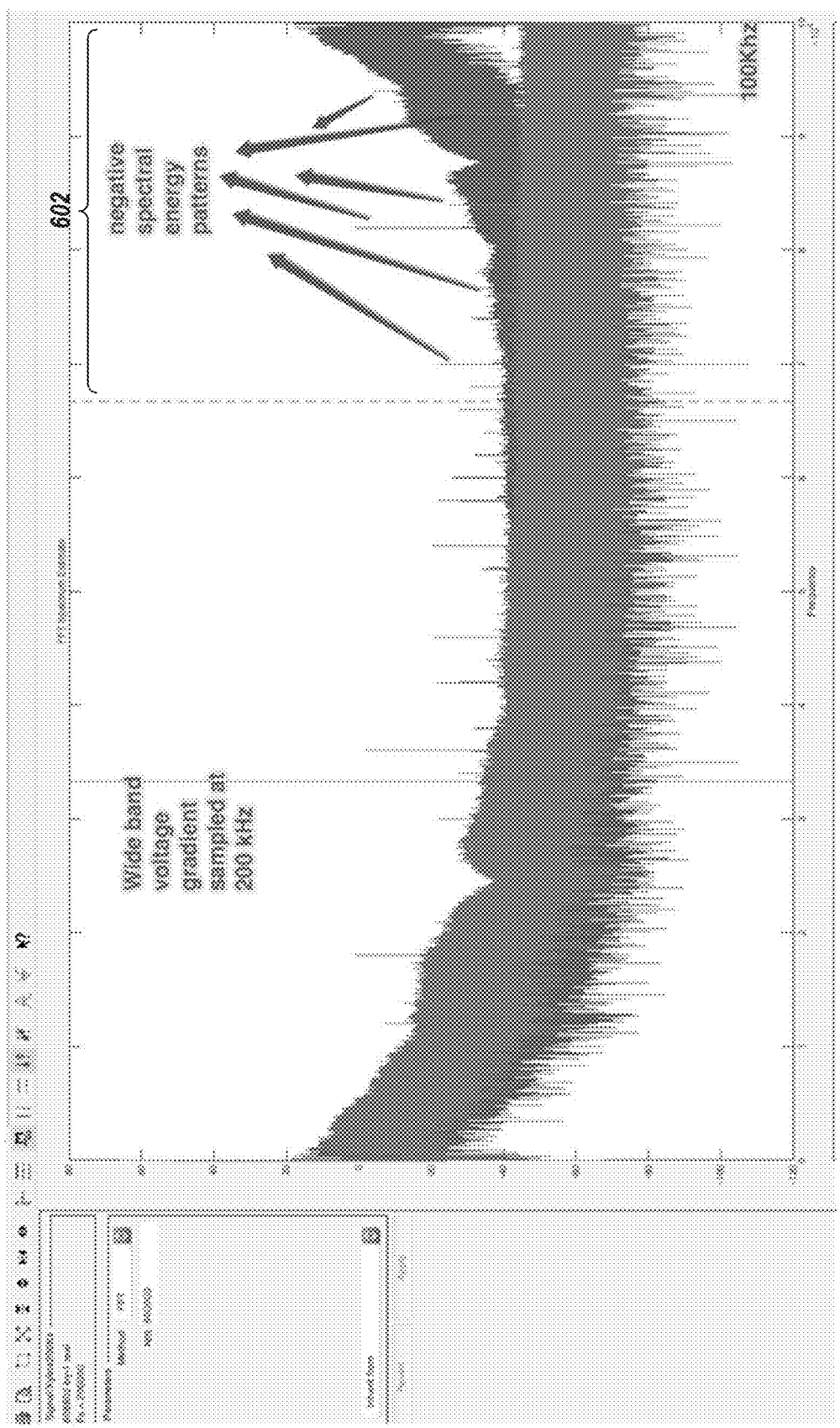
FIG. 6 is a frequency plot of an example ultra-wide-band cardiac gradient signal associated with three surface electrodes, in accordance with an illustrative embodiment.

FIG. 6 is a frequency plot of an example ultra-wide-band cardiac gradient signal, in accordance with an illustrative embodiment. As shown, FIG. 6 is sampled at a frequency of about 200 kHz and includes frequency components of an ultra-wide-band cardiac gradient signal up to about 100 kHz (according to the Nyquist sampling theorem). Notably, as shown, the presented ultra-wide-band cardiac gradient signal includes negative spectral energy signatures in frequencies greater than about 70-80 kHz (shown as frequencies 602); the negative spectral energy signatures, in the frequency domain, having energy between about 40 dB and about 50 dB. The data suggest that low-energy signatures in ultra-wide-band electrocardiograms may have information that could be used to image morphologies or functions of the body and/or for diagnostics.

Example Processing of Wide-Band Biopotential Signal Data

Figure 7:
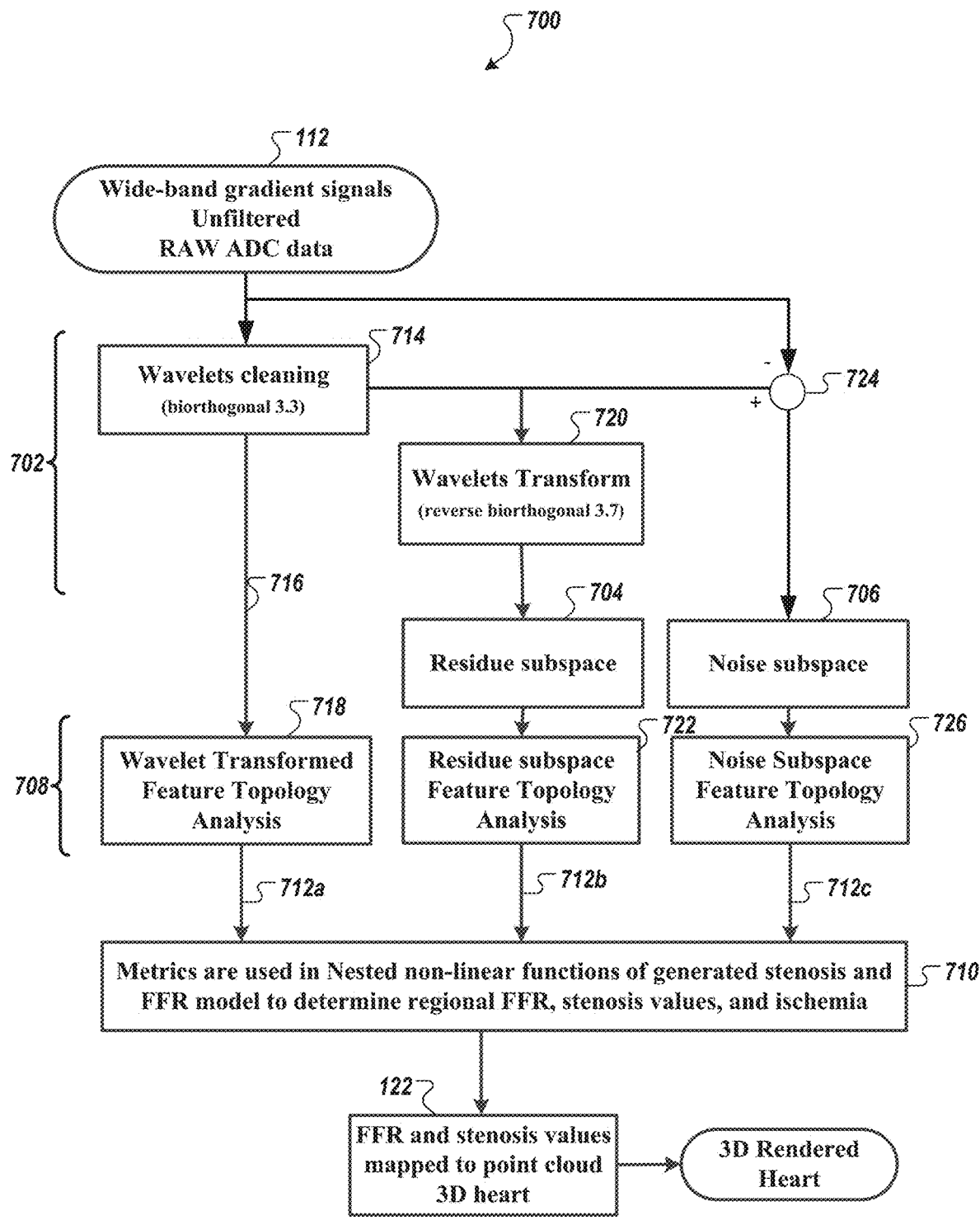
FIG. 7 is a diagram of a method of processing wide-band cardiac gradient signal to non-invasively identify and/or estimate a degree of myocardial ischemia, stenosis identification, and/or localization and fractional flow reserve estimation, in accordance with an illustrative embodiment.

FIG. 7 is a diagram of a method 700 of processing the wide-band biopotential signal data 112 (and ultra-wide-band biopotential signal data), in accordance with an illustrative embodiment. As shown in FIG. 7, the method 700 includes collecting the wide-band gradient cardiac signal data 112 (shown as "Wide-band gradient signals Unfiltered RAW ADC data" 112) and pre-processing 702 the wide-band gradient cardiac signal data to generate a phase space dataset (shown as "residue subspace" dataset 704 and "noise subspace" dataset 706) in phase space analysis, whereby features of the phase space dataset (704, 704) are extracted (operations 708) and evaluated in nested non-linear functions 710 to generate stenosis and FFR estimation values 122.

The wide-band gradient cardiac signal data 112 may be collected from one or more electrodes (e.g., surface electrodes, non-contact electrodes). In some embodiments, the wide-band gradient cardiac signal data 112 are simultaneously collected from between 1 and about 20 or more electrodes (e.g., 1 electrode, 2 electrodes, 3 electrodes, 4 electrodes, 5 electrodes, 6 electrodes, 7 electrodes, 8 electrodes, 9 electrodes, 10 electrodes, 11 electrodes, 12 electrodes, 13 electrodes, 14 electrodes, 15 electrodes, 16 electrodes, 17 electrodes, 18 electrodes, 19 electrodes, and 20 or more electrodes). In some embodiments, the sampling of these electrodes may have a less than a 10-femtosecond skew or "lag". In other embodiments, the sampling of these electrodes may have a less than a 100-femtosecond skew or lag. In other embodiments, the sampling of these electrodes may have a less than a few picosecond skew or lag. In some embodiments, the wide-band cardiac gradient signal 112 has a frequency component up to about 10 kHz (e.g., about 0 Hz to about 4 kHz; about 0 Hz to about 5 kHz; about 0 Hz to about 6 kHz; about 0 Hz to about 7 kHz; about 0 Hz to about 8 kHz; about 0 Hz to about 9 kHz; or about 0 Hz to about 10 kHz). In some embodiments, the wide-band cardiac gradient signal 112 has a frequency component up to about 50 kHz (e.g., about 0 Hz to about 50 kHz). In some embodiments, the wide-band gradient cardiac signal data 112 has a voltage resolution of about ½ μV sensitivity. In other embodiments, the wide-band cardiac gradient signal data 112 has a voltage resolution greater than about ½ μV sensitivity (e.g., about 1 μV, about 10 μV, about 100 μV, or about 1 mV). In some embodiments, the resolution of the signal data is about 24 bits. In some embodiments, the effective resolution is 20 bits, 21 bits, 22 bits, or 23 or more bits. In some embodiments, the effective resolution is less than 20 bits (e.g., 18 bits or 14 bits or fewer).

In some embodiments, the phase space plot analysis uses geometrical contrast that arises from the interference in the phase plane of the depolarization wave with any other orthogonal leads. The presence of noiseless subspaces allows the recording of the phase of these waves. In general, the amplitude resulting from this interference can be measured; however, the phase of these orthogonal leads still carries the information about the structure and generates geometrical contrast in the image. The phase space plot analysis takes advantage of the fact that different bioelectric structures within, e.g., the heart and its various types of tissue have different impedances, and so spectral and non-spectral conduction delays and bends the trajectory of phase space orbit through the heart by different amounts. These small changes in trajectory can be normalized and quantified beat-to-beat and corrected for abnormal or poor lead placement and the normalized phase space integrals can be visualized on, or mapped to, a geometric mesh using a genetic algorithm to map 17 myocardial segments in the ventricle to various tomographic imaging modalities of the heart from retrospective data.

Referring still to FIG. 7, three separate phase space analyses are performed to generate sets of metrics and variables (shown as 712a, 712b, and 712c) to be used in the non-linear functions 710 to generate regional FFR estimation values, regional stenosis values, and regional ischemia values 122. Table 1 is an example output matrix 122.

TABLE 1

| Segment | Vessel | FFR | Stenosis | Ischemia |
|---|---|---|---|---|
| 1 | Left Main Artery (LMA) | 0.90 | 0.50 | 0.20 |
| 2 | Proximal Left Circumflex Artery (Prox LCX) | 0.85 | 0.60 | 0.30 |
| 3 | Mid- Left Circumflex Artery (Mid LCX) | 0.93 | 0.35 | 0.15 |
| 4 | Distal Left Circumflex Artery (Dist LCX) | 1.00 | 0.00 | 0.00 |
| 5 | Left Posterior Atrioventricular (LPAV) | 1.00 | 0.00 | 0.00 |
| 6 | First Obtuse Marginal (OM1) | 0.60 | 0.95 | 0.72 |
| 7 | Second Obtuse Marginal (OM2) | 1.00 | 0.00 | 0.00 |
| 8 | Third Obtuse Marginal (OM3) | 1.00 | 0.00 | 0.00 |
| 9 | Proximal Left Anterior Descending Artery (Prox LAD) | 1.00 | 0.00 | 0.00 |
| 10 | Mid Left Anterior Descending Artery (Mid LAD) | 1.00 | 0.00 | 0.00 |
| 11 | Distal Left Anterior Descending Artery (Dist LAD) | 0.70 | 0.80 | 0.63 |
| 12 | LAD D1 | 0.00 | 0.00 | 0.75 |
| 13 | LAD D2 | 0.00 | 0.00 | 0.00 |

TABLE 1-continued

| Segment | Vessel | FFR | Stenosis | Ischemia |
|---|---|---|---|---|
| 14 | Proximal Right Coronary Artery (Prox RCA) | 0.00 | 0.00 | 0.00 |
| 15 | Mid Right Coronary Artery (Mid RCA) | 0.00 | 0.00 | 0.00 |
| 16 | Distal Right Coronary Artery (Dist RCA) | 0.00 | 0.00 | 0.18 |
| 17 | Acute Marginal Brach Right of the Posterior Descending Artery (AcM R PDA) | 0.00 | 0.00 | 0.00 |

As shown, Table 1 includes a fractional flow reserve (FFR) parameter, an estimated stenosis parameter, and an estimated ischemia parameter for a plurality of segments corresponding to major vessels in the heart. In some embodiments, the matrix 122 includes a fractional flow reserve (FFR) parameter, an estimated stenosis parameter, and an estimated ischemia parameter for a standardized myocardial segment map having 17 segments of the heart including the Left Main Artery (LMA), the Proximal Left Circumflex Artery (Prox LCX), the Mid-Left Circumflex Artery (Mid LCX), the Distal Left Circumflex Artery (Dist LCX), the Left Posterior Atrioventricular (LPAV), the First Obtuse Marginal Branch (OM1), the Second Obtuse Marginal Brach (OM2), the Third Obtuse Marginal Branch (OM3), the Proximal Left Anterior Descending Artery (Prox LAD), the Mid Left Anterior Descending Artery (Mid LAD), the Distal Left Anterior Descending Artery (Dist LAD), the Left Anterior Descending First Diagonal Branch (LAD D1), the Left Anterior Descending Second Diagonal Branch (LAD D2), the Proximal Right Coronary Artery (Prox RCA), the Mid Right Coronary Artery (Mid RCA), the Distal Right Coronary Artery (Dist RCA), and the Acute Marginal Brach Right of the Posterior Descending Artery (AcM R PDA). In Table 1, the parameters for myocardial ischemia estimation, stenosis identification, and/or fractional flow reserve estimation are shown in a range of 0 to 1. Other scaling or ranges may be used.

Example Nested Functions to Generate Fractional Flow Reserve (FFR) Estimation

Tables 2-5 show example non-linear functions to generate FFR estimations for several segments corresponding to major vessels in the heart. In Table 2, an example function to determine a FFR estimation for the left main artery ("FFR_LEFTMAIN") is provided.

TABLE 2

| FFR_LEFTMAIN = 0.128467341682411*noisevectorRz*atan2(Alpharatio, DensityV4) |
|---|

As shown in Table 2, the FFR estimation for the left main artery is determined based on extracted metrics and variables such as a Z-component parameter associated with the noise subspace 706 ("noisevectorRz"), a Alphahull ratio parameter ("Alpharatio"), and a signal density cloud volume 4 ("DensityV4").

In Table 3, an example function to determine a FFR estimation for the mid right coronary artery ("FFR_MIDRCA") is provided.

TABLE 3

| FFR_MIDRCA = 0.0212870065789474*noisevectorRy*Alpharatio*DensityV3 |
|---|

As shown in Table 3, the FFR estimation for the mid right coronary artery is determined based on extracted metrics and variables such as a Y-component parameter associated with the noise subspace 706 ("noisevectorRy"), the Alphahull ratio parameter ("Alpharatio"), and a signal density cloud volume 3 ("DensityV3").

In Table 4, an example function to determine a FFR estimation for the mid left artery descending ("FFR_MID-LAD") is provided.

TABLE 4

FFR_MIDLAD = atan2(AspectRatio3, residueLevelMean)

As shown in Table 4, the FFR estimation for the mid left artery descending is determined based on extracted metrics and variables such as a ratio of volume to surface area for cloud cluster 3 ("AspectRatio3") and a wavelet residue mean XYZ ("residueLevelMean").

In Table 5, an example function to determine a FFR estimation for the proximal left circumflex artery ("FFR_PROXLCX") is provided.

TABLE 5

FFR_PROXLCX = 0.408884581034257*atan2(residueLevelVolume + vectorcloud6, DensityV4)

As shown in Table 5, the FFR estimation for the proximal left circumflex artery is determined based on extracted metrics and variables such as a wavelet residue volume XYZ ("residueLevelVolume"), vector cloud 6 volume ("vectorcloud6"), and a signal density cloud volume 4 ("DensityV4").

Example Wavelet Cleaning Operator

Referring again to FIG. 7, a wavelet operator 714 (shown as "wavelets cleaning" 714) can perform an operation on the wide-band gradient signal data 112 (or a derived data therefrom). It should be understood to those skilled in the art that other intermediate phase linear processing may be perform on the signal data 112 prior to operation by the wavelet operator 714. In some embodiments, the wavelet operator 714 comprises a Biorthogonal wavelet 3.3 transform. FIGS. 10A and 10B are diagrams of an example wavelet transformation (i.e., Biorthogonal wavelet 3.3) used to generate a multi-dimensional wavelet-cleansed dataset, in accordance with an illustrative embodiment. FIG. 10A shows a decomposition scaling function φ. FIG. 10B shows a decomposition wavelet function ψ. FIG. 11 is a diagram of an example output 1102 of the wavelet cleaning operation. The output 1102 is show in conjunction with the input 1104 to the wavelet cleaning operation. The output, in some embodiments, is a time series dataset.

Referring still to FIG. 7, the output of the wavelet operator 714 is combined and transformed, via phase space transformation 718, to produce the multi-dimensional wavelet-cleansed dataset 716. Feature topology analysis (also shown in block 718) is performed on the multi-dimensional wavelet-cleansed dataset 716 to extract metrics and variables 712a. The extracted metrics and variables 712a, in some embodiments, include morphological, topologic, or functional features of the multi-dimensional wavelet-cleansed dataset including, for example, 3D volume value, a void volume value, a surface area value, a principal curvature direction value, and a Betti number value. In some embodiments, the multi-dimensional wavelet-cleansed dataset may be segmented, or partitioned, into sub-regions to which metrics and variables of these sub-regions are extracted. In some embodiments, a void volume value, a surface area value, a principal curvature direction value, and a Betti number value is also determined for each sub-region. In some embodiments, the number of generated sub-regions (also referred to as number of segment) is between about 2 and about 20 (e.g., 2, 3, 4, 5, 6, 7, 8, 9, 10, 11, 12, 13, 14, 15, 16, 17, 18, 19, and 20). In some embodiments, the number of sub-regions is greater than 20.

Figure 8:
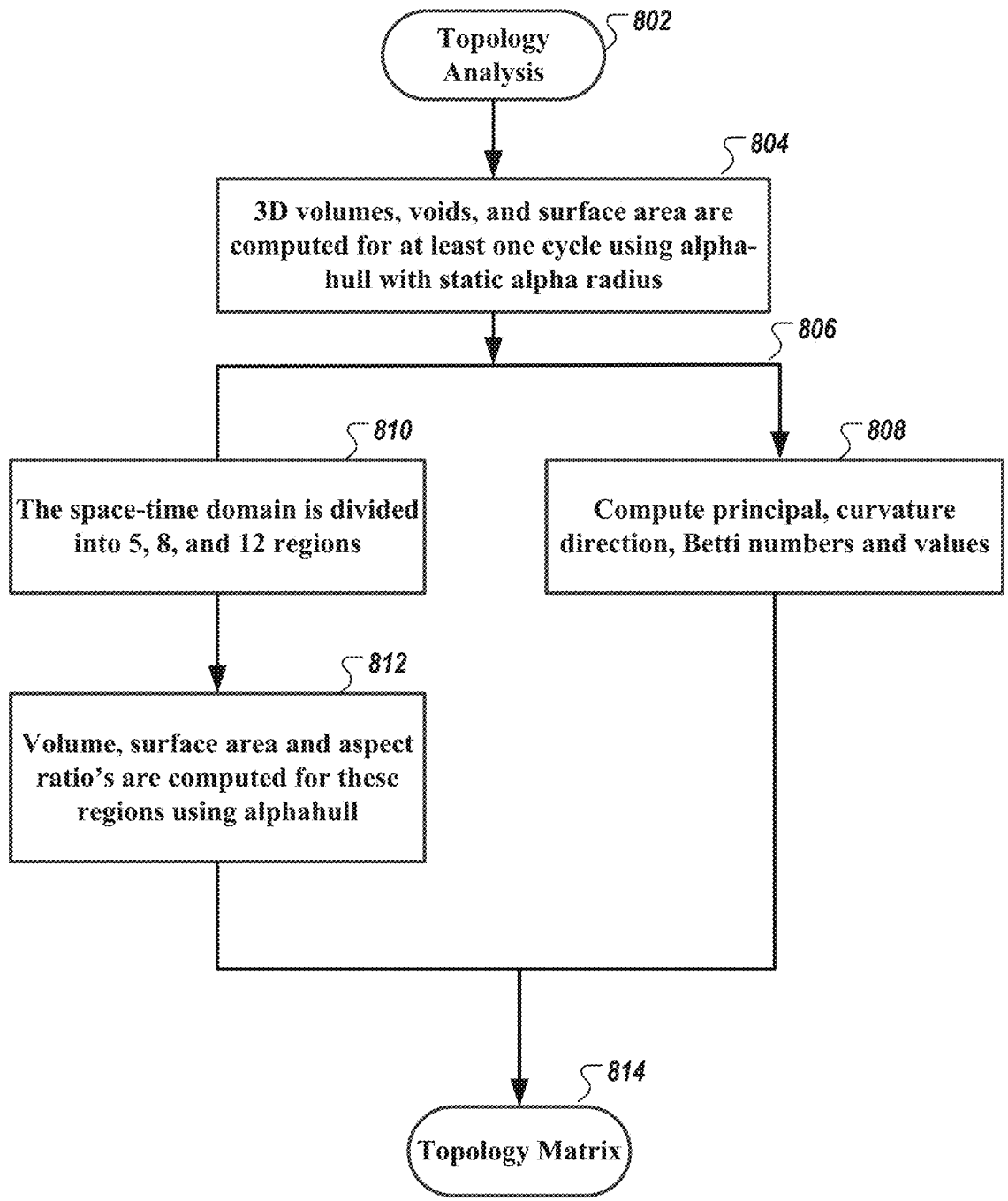
FIG. 8 is a diagram of a method of performing feature topology analysis, e.g., of a multi-dimensional residue subspace dataset, a multi-dimensional noise subspace dataset, and a multi-dimensional wavelet cleansed dataset, in accordance with an illustrative embodiment.

FIG. 8 is a diagram of a method 800 of performing feature topology analysis of the multi-dimensional wavelet-cleansed dataset. In some embodiments, the method 800 may be similarly performed on other datasets, such as the multi-dimensional noise subspace dataset 712b and multi-dimensional wavelet-cleansed dataset 712c generated by each of the phase space analyses (e.g., residue subspace analysis and noise subspace analysis) as described in relation to FIG. 7. As shown in FIG. 8, a morphological, topologic, or functional feature extraction analysis (shown as "Topology Analysis" 802) includes, in some embodiments, computing 3D volumes, voids, and surface area for at least one cycle of the multi-dimensional wavelet-cleansed dataset as a space-time domain dataset using an alpha-hull operator 804. In some embodiments, the alpha-hull operator uses a static alpha radius. Further detail of the alpha-hull operator is described in Edelsbrunner et al., "Three-dimensional alpha shapes," ACM Transactions on Graphics, Vol. 13 (1): 43-72 (1994), which is incorporated by reference herein in its entirety. Other topologic or geometric encapsulation operations may be used, including, for example, but not limited to Delauney triangulation. Delaunay triangulations are triangulations on a set of points such that no point is within the circumcircle of any triangle in the triangulation, and the minimum angle of all the angles in each triangle in the triangulation is maximized.

Referring still to FIG. 8, the generated multi-dimensional output of the alpha-hull operator 806 may be further extracted to compute (operator 808) principal direction, curvature direction, Betti numbers, and Betti values. In addition, the dataset as a space-time domain dataset is further segmented (via operator 810) into sub-regions and volume, surface area and aspect ratios are computed for these sub-regions also using an alphahull operator 812. As shown, the space-time domain dataset is segmented into 5 regions, 8 regions, and 12 regions to which volume, surface area and aspect ratio parameters are computed for some of all of these regions. In some embodiments, the three group of regions comprising 25 regions may generate 3 parameters for each regions to provide 75 metrics or variables 712a. In combination with the computed volume, surface area, and aspect ratios of the alphahull output and the principal direction, curvature direction, Betti numbers, and Betti values thereof, there may be 82 metrics or variables 712a. The metrics and variables 712a may be provided as a matrix (shown as a "topology matrix" 814).

It should be appreciated that other topologic features may be extracted in addition, or in substitute, those discussed herein. These features may include properties such as energy, surface variations, etc., or geometric features such as size.

It should be appreciated that other metrics and variables may be extracted and used depending on the number of operations performed and that the example provided herein is merely for illustrative purposes.

Example Residue Subspace Analysis and Topology Extraction

Referring again to FIG. 7, attention is directed to a second phase space analysis performed to determine metrics and variables 712b for a multi-dimensional residue subspace dataset 704.

FIG. 12 is a diagram of an example wavelet-based operation 1202 to generate the multi-dimensional residue subspace dataset 704 as described in relation to FIG. 7, in accordance with an illustrative embodiment. As shown in both FIGS. 7 and 12, multi-dimensional residue subspace dataset 704 is generated as a residue (e.g., a subtraction operator 1202 in FIG. 12) of two wavelet operators (e.g., 714 and 720). The first wavelet operator may be the wavelets cleaning 714, for example, using the biorthogonal wavelet 3.3 operator. The second wavelet operator may be a Reverse Biorthogonal Wavelet 3.7 operator 720.

FIGS. 13A and 13B are diagrams of an example wavelet transformation (i.e., Reverse Biorthogonal wavelet 3.7) used to generate a multi-dimensional residue subspace dataset, in accordance with an illustrative embodiment. FIG. 13A shows a decomposition scaling function φ. FIG. 13B shows a decomposition scaling function ψ. It should be that other phase linear wavelet operators may be used.

Referring still to FIG. 7, each residue output of the wavelet operator 714 and wavelet operator 720 for each of the gradient signals are combined and transformed, via phase space transformation, to produce the multi-dimensional residue subspace dataset 704. Feature topology analysis (also shown in block 722) is performed on the multi-dimensional wavelet residue dataset to extract metrics and variables 712b. The extracted metrics and variables 712b may include morphological, topologic, or functional features of the multi-dimensional wavelet residue dataset including, for example, 3D volume value, a void volume value, a surface area value, a principal curvature direction value, and a Betti number value. In some embodiments, the multi-dimensional wavelet cleansed dataset may be segmented, or partitioned, into sub-regions to which metrics and variables of these sub-regions are extracted. In some embodiments, a void volume value, a surface area value, a principal curvature direction value, and a Betti number value is also determined for each sub-region. In some embodiments, the number of generated sub-regions (also referred to as number of segment) is between 2 and about 20 (e.g., 2, 3, 4, 5, 6, 7, 8, 9, 10, 11, 12, 13, 14, 15, 16, 17, 18, 19, and 20). In some embodiments, the number of sub-regions is greater than 20. In some embodiments, a similar or same topology extraction analysis as described in relation to FIG. 8 may be performed.

Figure 14:
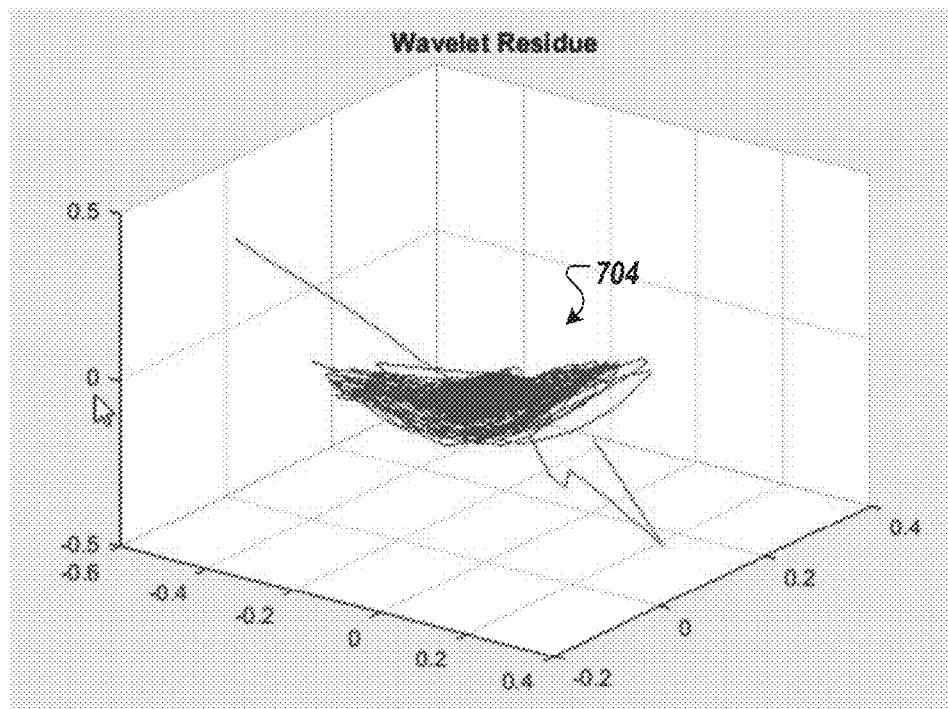
FIG. 14 is a depiction of an example multi-dimensional residue subspace dataset, in accordance with an illustrative embodiment.

FIG. 14 is a depiction of an example residue subspace 704 which results from subtracting wavelet models (e.g., 714 and 720) using biorthogonal 3.3 and reverse biorthogonal 3.7 operations. The residue subspace represents parts of the biological signal that are effectively too complex and non-linear to fit (i.e., represented) with a single wavelet function. This residue subspace is processed, transformed into representative features, and used to study the dynamical and geometrical properties of the cardiac gradient data.

Figure 16:
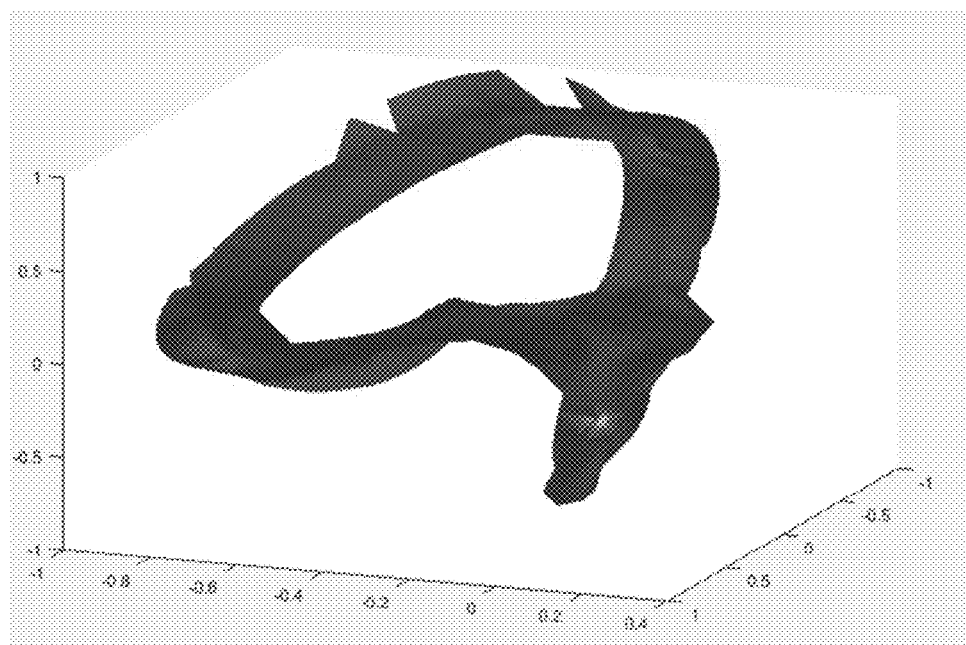
FIGS. 16 and 17 are each a depiction of an example multi-dimensional residue subspace dataset, in accordance with an illustrative embodiment.

FIG. 16 is a depiction of an example dynamical phase space volume object that has been colored by the residue subspace. The phase space volume object is generated by overlaying the value of the residue subspace as a color intensity mapping upon the input wide-band gradient signal data. The lack of intensive coloring is indicative of the absence of ischemic myocardial tissue. That is, FIG. 16 is an example dynamical phase space volume object of a healthy person.

Figure 17:
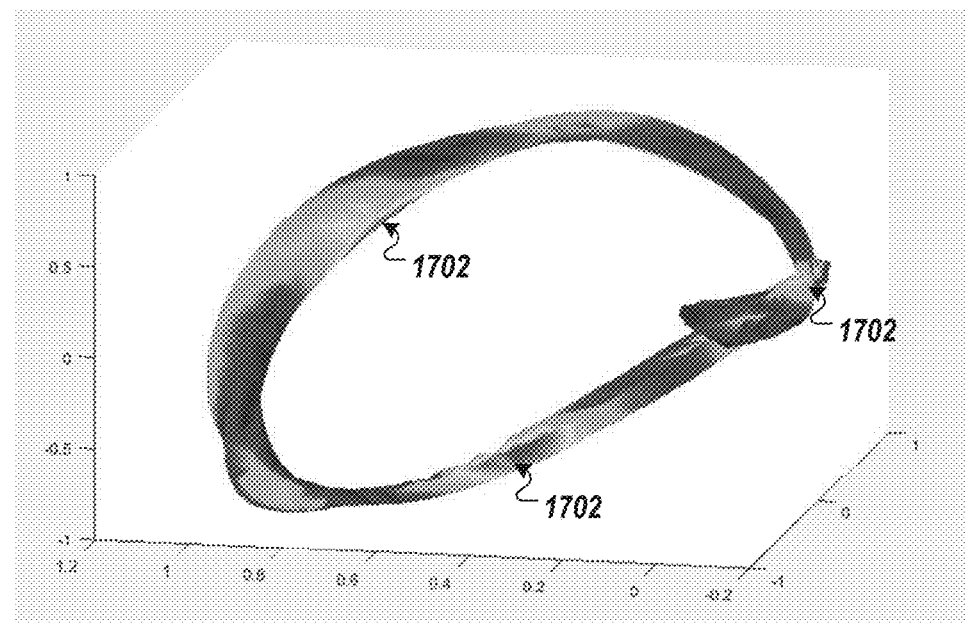

FIG. 17 is a depiction of an example dynamical phase space volume object associated with an ischemic patient. That is, the dynamical phase space volume object was generated using wide-band gradient signal data of a patient diagnosed with an ischemic myocardium. The dynamical phase space volume object has been colored by the residue subspace by overlaying the value of the residue subspace as a color intensity mapping upon the input wide-band gradient signal data. The intensive coloring (corresponding to arrow 1702) is indicative of the presence of an ischemic myocardium.

Example Noise Subspace Analysis and Topology Extraction

Referring again to FIG. 7, attention is directed to a third phase space analysis performed to determine metrics and variables 712c for a multi-dimensional noise subspace dataset 706. As shown in FIG. 7, the multi-dimensional noise subspace dataset 706 may be computed by subtracting, via a subtraction operator 724, the input wide-band gradient signal data 112 (or a dataset derived therefrom) and the output of the wavelet cleansed signal data 716. The outputs of the subtraction operation are combined and transformed, via phase space transformation, to produce the multi-dimensional residue subspace dataset 706. Feature topology analysis (also shown in block 726) is performed on the multi-dimensional noise subspace dataset to extract metrics and variables 712c. The extracted metrics and variables 712c may include morphological, topologic, or functional features of the multi-dimensional wavelet residue dataset including, for example, 3D volume value, a void volume value, a surface area value, a principal curvature direction value, and a Betti number value. In some embodiments, the multi-dimensional wavelet cleansed dataset may be segmented, or partitioned, into sub-regions to which metrics and variables of these sub-regions are extracted. In some embodiments, a void volume value, a surface area value, a principal curvature direction value, and a Betti number value is also determined for each sub-region. In some embodiments, the number of generated sub-regions (also referred to as number of segments) is between 2 and about 20 (e.g., 2, 3, 4, 5, 6, 7, 8, 9, 10, 11, 12, 13, 14, 15, 16, 17, 18, 19, and 20). In some embodiments, the number of sub-regions is greater than 20. In some embodiments, a similar or same topology extraction analysis as described in relation to FIG. 8 may be performed.

Figure 15:
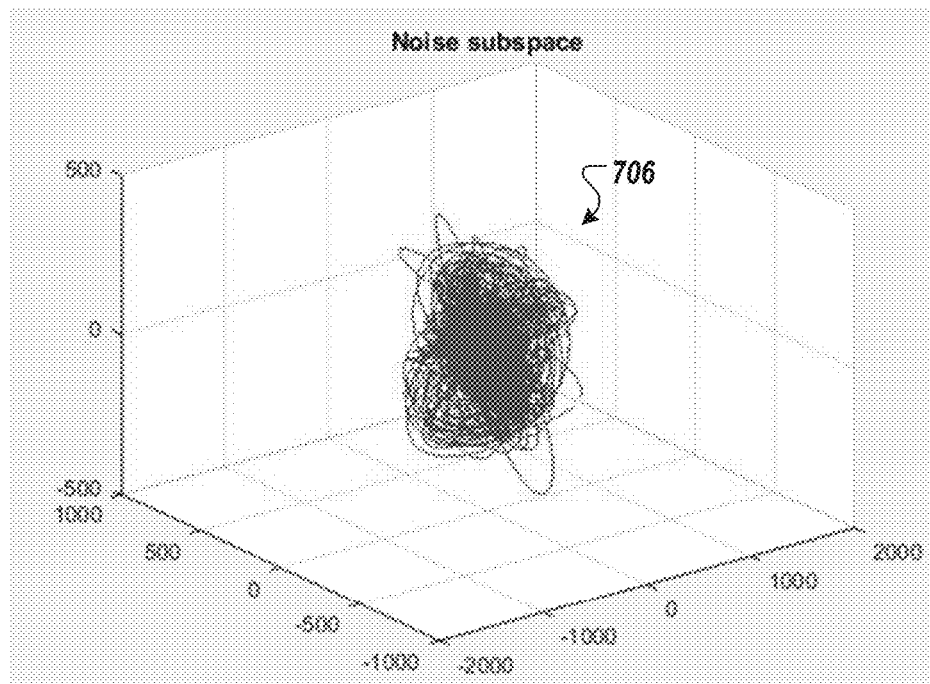
FIG. 15 is a depiction of an example multi-dimensional noise subspace dataset, in accordance with an illustrative embodiment.

FIG. 15 is a depiction of the noise subspace 706, which is the result of subtracting a biorthogonal 3.3 wavelet model (e.g., 714) from the input wide-band gradient data 112. Similar to the residue subspace 704, it contains complex dynamical information. Specifically, the noise subspace contains chaotic information that cannot be effectively captured in a model. This noise subspace is processed, transformed into representative features, and used to study the dynamical and geometrical properties of the cardiac gradient data.

Figure 18:
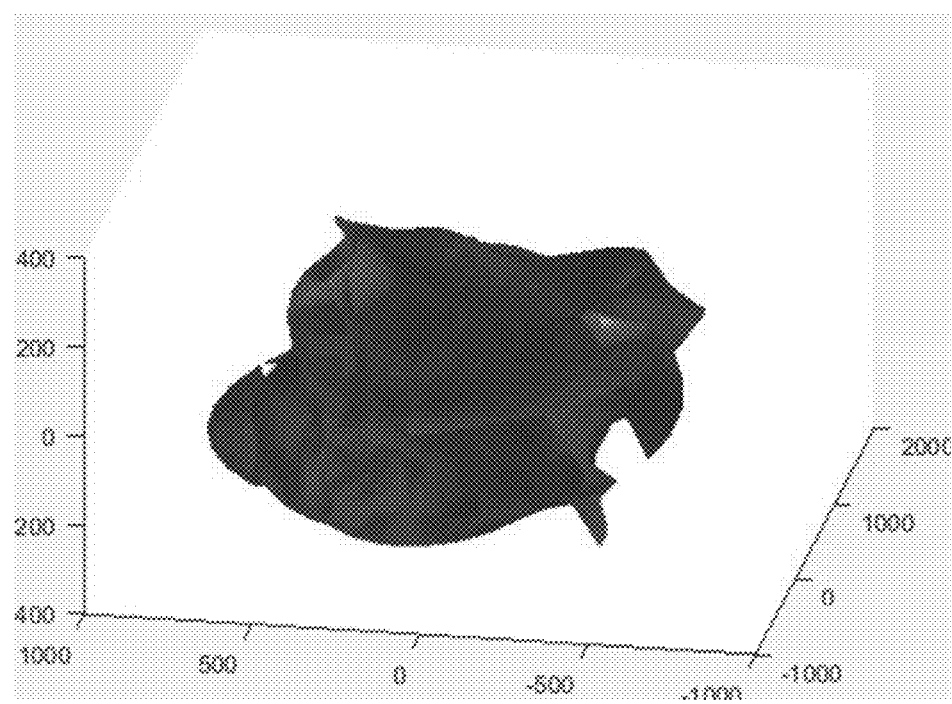
FIGS. 18 and 19 are each a depiction of an example multi-dimensional noise subspace dataset, in accordance with an illustrative embodiment.

FIG. 18 is a depiction of an example noise subspace phase space object that has been colored by the noise subspace. The phase space object is generated by overlaying the value of the noise subspace as a color intensity mapping upon a derivative transformation (e.g., a numeric fractional derivative) of the input wide-band gradient signal data (or a derived data thereof). As shown in FIG. 18, the lack of intensive coloring is indicative of the absence of an ischemic myocardium. That is, FIG. 18 is an example noise subspace phase space object of a healthy person.

Figure 19:
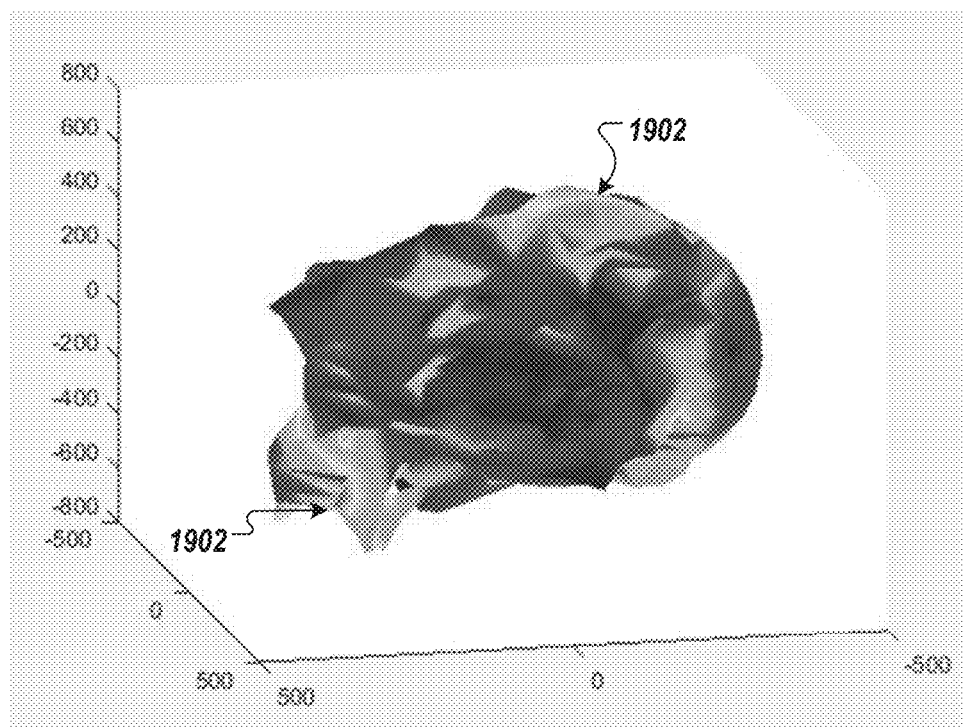

FIG. 19 is a depiction of an example noise subspace phase space object associated with an ischemic patient. The phase space object has been colored by the noise subspace by overlaying the value of the noise subspace as a color intensity mapping upon a derivative transformation (e.g., a numeric fractional derivative) of the input wide-band gradient signal data (or a derived data thereof). The intensive coloring (corresponding to arrow 1902) is indicative of the presence of an ischemic myocardium.

Example Machine Learning Analysis

Figure 9:
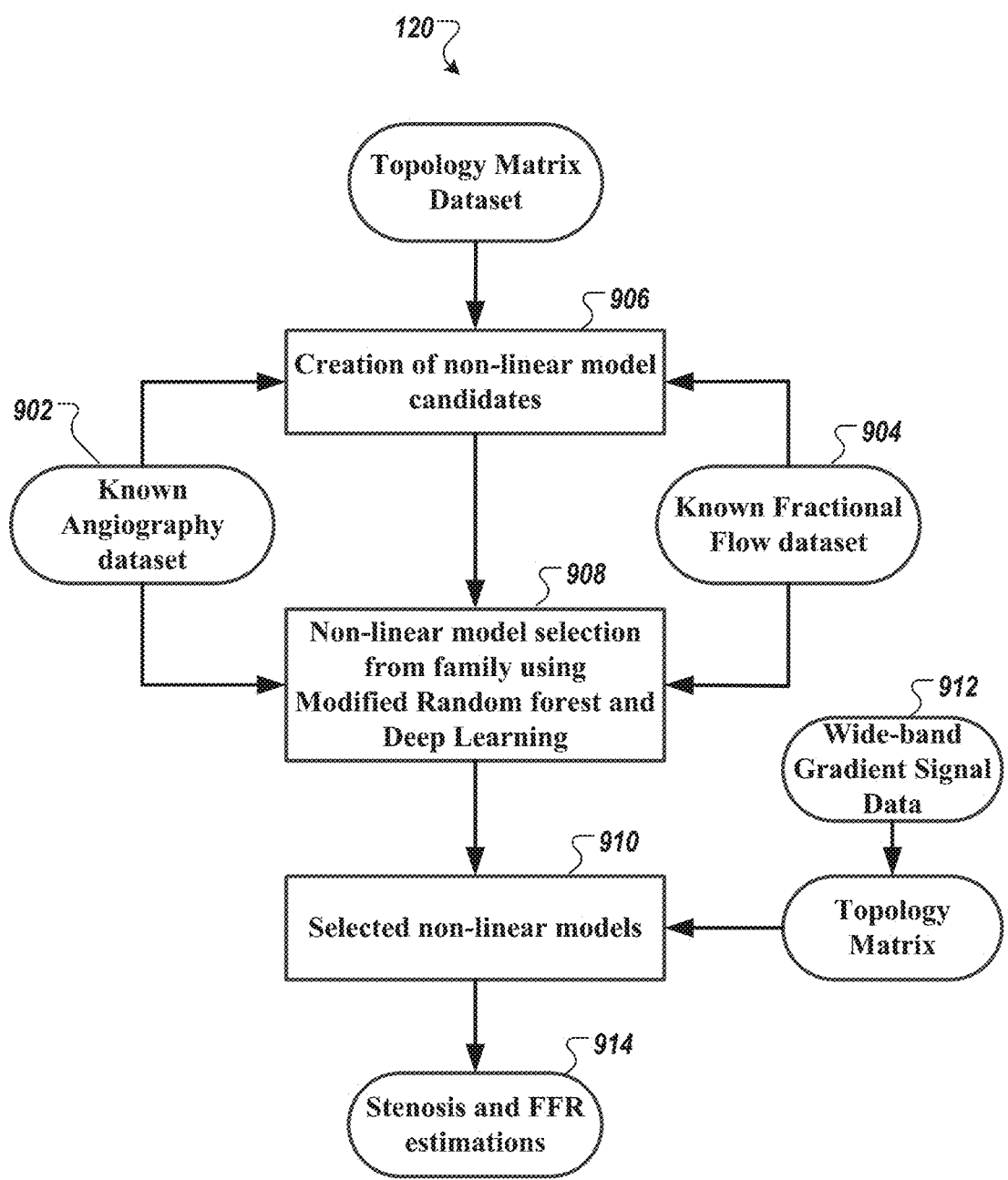
FIG. 9 is a diagram of a method of performing machine learning analysis to create and select non-linear models to identify and/or estimate a degree of myocardial ischemia, stenosis identification, and/or localization and fractional flow reserve estimation, as described in relation to FIG. 8, in accordance with an illustrative embodiment.

FIG. 9 is a diagram of a method of performing machine learning analysis to create and select non-linear models to identify and/or estimate a degree of myocardial ischemia, identify one or more stenoses, and/or localize and/or estimate fractional flow reserve, as described in relation to FIG. 8, in accordance with an illustrative embodiment. As shown in FIG. 9, angiographic dataset 902 and fractional flow dataset 904 are used to create (via operation 906) candidate non-linear models to identify stenosis (and/or estimate a degree thereof) and estimate fractional flow reserve 914. Examples of the generation of non-linear models, e.g., to estimate cardiac chamber size and mechanical function, are described, for example, in U.S. application Ser. No. 14/295,615, titled "Noninvasive electrocardiographic method for estimating mammalian cardiac chamber size and mechanical function", which is incorporated by reference herein in its entirety.

In some embodiments, machine learning algorithms 908 are then used to select a family of non-linear models 910 from the candidate non-linear models using wide-band gradient cardiac signal data 912 of patients or subjects with some degree of stenosis and ischemia. In some embodiments, the machine learning algorithms are based on Regression Random Forest algorithms or a modified variation thereof. In some embodiments, the machine learning algorithms are based on deep learning algorithms.

In some embodiments, the machine learning phase invokes a meta-genetic algorithm to automatically select a subset of features drawn from a large pool. This feature subset is then used by an AdaBoost algorithm to generate predictors to diagnose significant coronary artery disease across a population of patients representing both positive and negative cases. The performances of the candidate predictors are determined through verification against a previously unseen pool of patients. Further description of the AdaBoost algorithm is provided in Freund, Yoav, and Robert E. Schapire, "A decision-theoretic generalization of on-line learning and an application to boosting," European conference on computational learning theory. Springer, Berlin, Heidelberg (1995), which is incorporated by reference herein in its entirety.

In some embodiments, space-time quantities can mapped to complex Phase Space differences in 12-dimensional space. Spatial changes in the phase space matrix can be extracted using a non-Fourier integral which creates the 12-dimensional space-time density metrics. These metrics for the ventricle are modeled using a genetic algorithm to link 17 nonlinear nested sinusoidal Gaussian equations, for the ventricles 17 Segments of the Coronary Arterial Territories, as perfusion blockages. Perfusion images were visually scored using a 17-segment model of the left ventricle and a 5-point scale (0=normal tracer uptake, 1=mildly reduced, 2=moderately reduced, 3=severely reduced, 4=no uptake). The amount of ischemic myocardial tissue (IM) was calculated as the summed difference score (the difference between summed stress and summed rest scores) divided by 80. Patients were classified as: no ischemia or equivocal (IM<5%), mild ischemia (5%≤IM<10%) and moderate/severe ischemia (IM≥10%). The output of these equations provides the amount and location of the ischemic myocardial tissue.

In some embodiments, the wide-band biopotential data 112 are operated upon with a modified matching pursuit (MMP) algorithm to create a sparse mathematical model. Detail of the MMP algorithm is provided in Mallat et al., "Matching Pursuits with Time-Frequency Dictionaries," *IEEE Transactions on Signal Processing*, Vol. 41 (12), Pages 3397-2415 (1993), the entirety of which is hereby incorporated by reference.

Characteristics of the model, including residue quantification, can be included in the feature set. The characteristics of the model may be extracted, in a feature extraction operation 706 (FIG. 7), to determine geometric and dynamic properties of the model. These subspaces may include, but are not limited to complex sub harmonic frequency (CSF) trajectory, quasi-periodic and chaotic subspaces, low/high energy subspaces, and fractional derivatives of the low/high energy subspaces. These subspaces are exemplars of the family of subspaces that characterize the dynamics of the system, whether pathological or normal.

Figure 20:
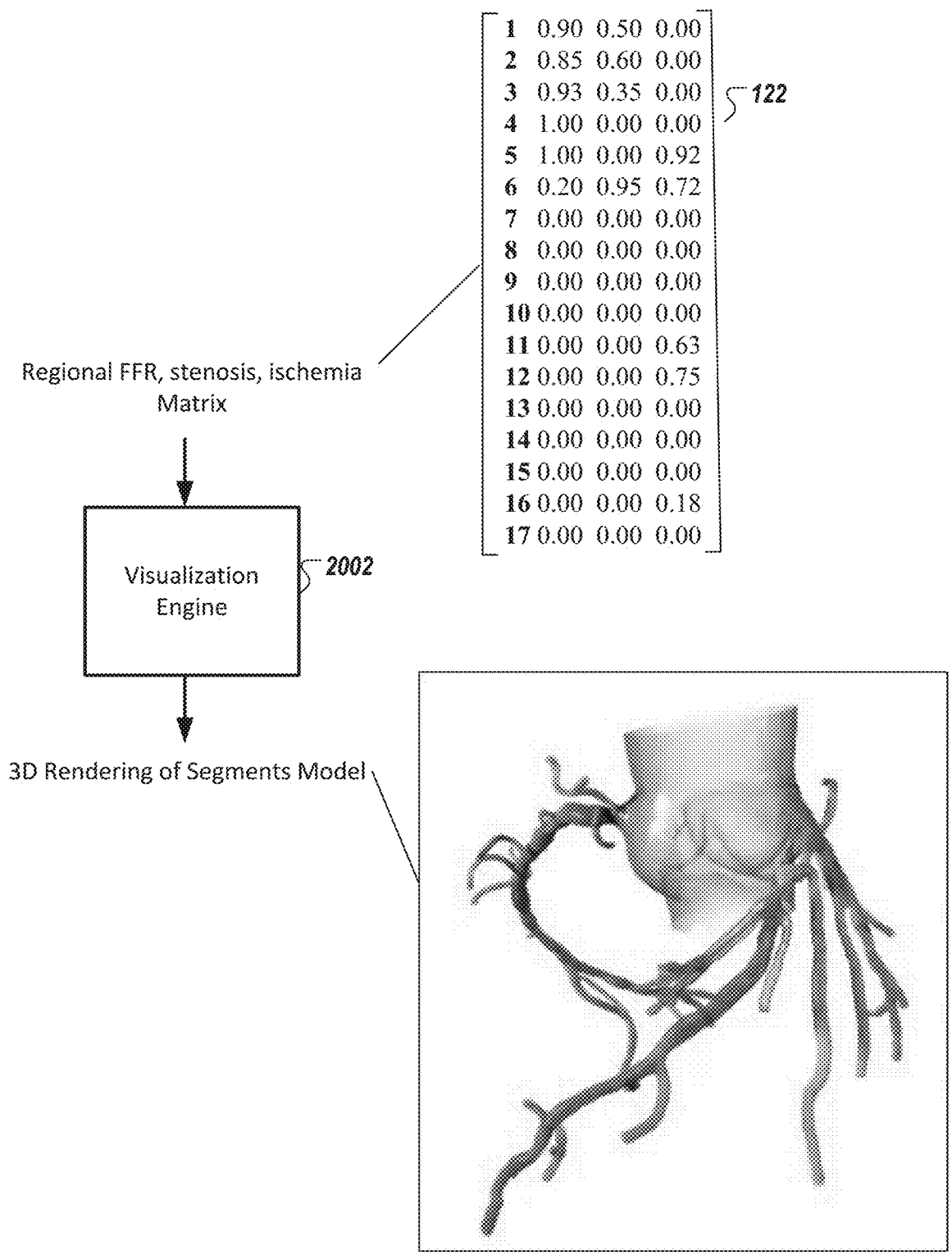
FIG. 20 is a diagram of a method of visualizing the determined arterial flow characteristics in the heart, in accordance with an illustrative embodiment.

FIG. 20 is a diagram of a method of visualizing the estimated arterial flow characteristics in the heart, in accordance with an illustrative embodiment. As shown in FIG. 20, a visualization engine 2002 receives the determined arterial flow characteristics and renders the characteristics onto a 3D visualization output. In some embodiments, the visualization engine 2002 provides, in a graphical user interface (GUI), a system-level view of all of the arterial flow characteristics and their interactions. In some embodiments, the GUI presents the cascading effects of upstream modifications to the arterial flow upon the downstream circulation.

Experimental Data

A coronary artery disease learning and formula development study conducted under a clinical protocol collects resting phase signals from human subjects prior to coronary angiography. The collected signals were evaluated using the non-invasive acquisition and analysis methods described herein to detect the presence of significant coronary artery disease in symptomatic adult patients or subjects. In addition, the collected signals were evaluated to assess the left ventricular ejection fraction and to identify the location of significant coronary artery disease. The performance of the non-invasive acquisition and analysis methods described herein were evaluated using a comparative paired trial design; the results are shown in FIGS. 21 and 22.

Further description of this clinical protocol is provided in U.S. Provisional Appl. No. 62/340,410, titled "Method and System for Collecting Phase Signals for Phase Space Tomography Analysis," which is incorporated by reference herein in its entirety.

FIGS. 21 and 22 are diagrams showing results of this study, which was conducted on 523 human subjects, in accordance with an illustrative embodiment. The presented data involves a prospective, non-randomized trial to refine the non-invasive acquisition and analysis methods described herein to detect and assess significant coronary artery disease (CAD) using paired phase signals with clinical outcomes data as assessed during a catheterization procedure (i.e., either a ≥70% stenosis or a reduced fractional flow rate of <0.80).

In the presented data, data sets (total of 523) of 429 subjects are used as the training data set, and data sets of 94 subjects are used as the verification population to assess sensitivity and specificity of non-invasive acquisition and analysis methods described herein. For a candidate predictor A (FIG. 21), the study provides a ROC curve of 0.80 with a positive predictor value (PPV) of 47% and a negative predictor value (NPV) of 96% as compared to angiography results. For a candidate predictor B (FIG. 22), the study provides a ROC curve of 0.78 with a positive predictor value (PPV) of 49% and a negative predictor value (NPV) of 92% as compared to angiography results. Candidate predictors A and B are internal parameters (such as training classifiers) used in the machine training process.

As compared with diagnostic performance of non-invasive myocardial perfusion imaging using single-photon emission computed tomography, cardiac magnetic resonance, and positron emission tomography for the detection of obstructive coronary artery disease as published in J. Am. Coll. Cardiol. 8:59(19), 1719-28 (May 2012) (shown as "SPECT"), the non-invasive acquisition and analysis methods described herein (shown as "cPSTA") performs comparably well. These solutions regularly achieved AUC-ROC scores greater than 0.7 in the verification phase, performing as well or better than previous human-guided methods. Table 6 below shows diagnostic performance between that study and the study herein.

TABLE 6

| Test | # of studies | Sensitivity (95% CI) | Specificity (95% CI) | Diagnostic Odds Ratio |
| --- | --- | --- | --- | --- |
| SPECT | 105 | 88% (88-89) | 61% (59-62) | 15.31 (13-19) |
| cPSTA (predictor A) | 1 | 92% (74-100) | 62% (51-74) | 19 (0-60) |
| cPSTA (predictor B) | 1 | 84% (64-95) | 68% (57-79) | 11.2 (0-41) |

Having thus described several embodiments of the present disclosure, it will be rather apparent to those skilled in the art that the foregoing detailed disclosure is intended to be presented by way of example only, and is not limiting. Many advantages for non-invasive method and system for location of an abnormality in a heart have been discussed herein. Various alterations, improvements, and modifications will occur and are intended to those skilled in the art, though not expressly stated herein. These alterations, improvements, and modifications are intended to be suggested hereby, and are within the spirit and the scope of the present disclosure. Additionally, the recited order of the processing elements or sequences, or the use of numbers, letters, or other designations therefore, is not intended to limit the claimed processes to any order except as may be specified in the claims. Accordingly, the present disclosure is limited only by the following claims and equivalents thereto.

For example, further examples of phase space processing that may be used with the exemplified method and system are described in U.S. Provisional Patent Application No. 62/184,796, title "Latent teratogen-induced heart deficits are unmasked postnatally with mathematical analysis and machine learning on ECG signals"; U.S. patent application Ser. No. 15/192,639, title "Methods and Systems Using Mathematical Analysis and Machine Learning to Diagnose Disease"; U.S. patent application Ser. No. 14/620,388, published as US2015/0216426, title "Method and system for characterizing cardiovascular systems from single channel data"; U.S. patent application Ser. No. 14/596,541, issued as U.S. Pat. No. 9,597,021, title "Noninvasive method for estimating glucose, glycosylated hemoglobin and other blood constituents"; U.S. patent application Ser. No. 14/077,993, published as US2015/0133803, title "Noninvasive electrocardiographic method for estimating mammalian cardiac chamber size and mechanical function"; U.S. patent application Ser. No. 14/295,615, title "Noninvasive electrocardiographic method for estimating mammalian cardiac chamber size and mechanical function"; U.S. patent application Ser. No. 13/970,582, issued as U.S. Pat. No. 9,408,543, title "Non-invasive method and system for characterizing cardiovascular systems and all-cause mortality and sudden cardiac death risk"; U.S. patent application Ser. No. 15/061,090, published as US2016/0183822, title "Non-invasive method and system for characterizing cardiovascular systems"; U.S. patent application Ser. No. 13/970,580, issued as U.S. Pat. No. 9,289,150, title "Non-invasive method and system for characterizing cardiovascular systems"; U.S. Patent Application No. 62/354,668, titled "Method and System for Phase Space Analysis to Determine Arterial Flow Characteristics"; and U.S. Provisional Patent Application No. 61/684,217, title "Non-invasive method and system for characterizing cardiovascular systems", which are each incorporated by reference in its entirety.

While the methods and systems have been described in connection with preferred embodiments and specific examples, it is not intended that the scope be limited to the particular embodiments set forth, as the embodiments herein are intended in all respects to be illustrative rather than restrictive.

For example, the exemplified methods and systems may be used generate stenosis and FFR outputs for use with interventional system configured to use the FFR/stenosis outputs to determine and/or modify a number of stents and their placement intra operation.

In addition, the exemplified methods and systems maybe used to quantify the risk of serious arrhythmias, sudden cardiac death, or other modes of death and all-cause mortality events in mammals.

Various phase space techniques and analyses may be performed to generate clinically useful information for assessing the state of the patient's health as well as to, e.g., pinpoint and distinguish disease states and their status as well as for predicting possible disease onset, whether it be in the cardiac or brain fields (such as when wide-band cardiac or cerebral phase gradient signals are used), the oncological field, the prenatal field, or any other medical field.

In some embodiments, the exemplified methods and systems maybe used to monitor and record short- and long-term changes in glucose and glycated hemoglobin levels.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications are referenced. The disclosures of these publications in their entireties are hereby incorporated by reference into this application in order to more fully describe the state of the art to which the methods and systems pertain.

It will be apparent to those skilled in the art that various modifications and variations.

What is claimed is:

1. A system for detecting one or more cardiac pathologies of a human subject, comprising:
   an analysis system configured with computer readable instructions to retrieve an electrophysiological signal data set that (i) is associated with the subject and (ii) has been acquired by measuring equipment configured to non-invasively capture, via one or more sensors, the signal data set as a long cardiac gradient record that exhibits complex non-linear variability, the analysis system using the signal data set to detect the one or more cardiac pathologies of the subject,
   wherein the detection operation comprises:
      generating, by a processor executing a transformation operation, an intermediate residue data set from the signal data set, wherein the intermediate residue data set comprises an alpha shape or a Delaunay triangle mesh data object of the signal data set; and
      generating, by the processor, one or more geometric features and/or dynamical properties of the alpha shape or the Delaunay triangle mesh, wherein the geometric features and/or the dynamical properties include at least one of:
         a 3D volume value,
         a void value,
         a surface area value,
         a principal curvature direction value, and
         a Betti number value,
      of the alpha shape or the Delaunay triangle mesh,
   wherein the generated one or more geometric features and/or dynamical properties of the alpha shape or the Delaunay triangle mesh are used as variables representative of the subject in a machine learning operation to detect the one or more cardiac pathologies of the subject.

2. The system of claim 1, wherein the intermediate residue data set is generated by:
   generating, by the processor, a model of the signal data set;
   determining, by the processor, a residue data object between the model and the signal data set, wherein the alpha shape or a Delaunay triangle mesh data object is generated from the residue data object of the signal data set.

3. The system of claim 1, wherein the signal data set includes cardiac data acquired via two or more channels, each of a biopotential signal acquired over a plurality of heart beats as the long cardiac gradient record.

4. The system of claim 3, wherein the signal data set is acquired for at least 210 seconds, and wherein a portion of the long cardiac gradient record is modeled to generate the residue data object.

5. The system of claim 1, wherein the signal data set comprises a plurality of wide-band gradient signals simultaneously captured via a plurality of channels, including the two or more channels, and wherein a temporal lag or skew between each of the channels is less than about 10 femtoseconds.

6. The system of claim 5, wherein each of the plurality of wide-band gradient signals is unfiltered prior to, and during, the transformation operation, to generate the signal data set.

7. The system of claim 5, wherein each of the plurality of wide-band gradient signals comprises cardiac data that in a frequency domain have frequency components greater than about 1 kHz.

8. The system of claim 5, wherein each of the plurality of wide-band gradient signals comprises cardiac data that in a frequency domain have frequency components of at least 8 kHz.

9. The system of claim 1, wherein the one or more sensors comprise at least one of a surface electrode, an intracardiac electrode, and a non-contact electrode.

10. The system of claim 1, wherein the machine learning operation comprises an artificial neural network algorithm or a regression random forest algorithm.

11. The system of claim 1, wherein the measuring equipment is configured to transmit the signal data set over a network to the analysis system.

12. The system of claim 11, further comprising:
    a storage area network, wherein the measuring equipment is configured to transmit the signal data set over the network to the storage area network, and wherein the analysis system is configured to retrieve the acquired signal data set from the storage area network for analysis.

13. A method comprising:
    retrieving, by a processor, from a storage area network, an electrophysiological signal data set that (i) is associated with a human subject and (ii) has been acquired by measuring equipment configured to non-invasively capture, via one or more sensors, the signal data set as a long cardiac gradient record that exhibits complex non-linear variability; and
    detecting one or more cardiac pathologies of the subject using the signal data set, wherein the detection operation comprises:
        generating, by the processor executing a transformation operation, an intermediate residue data set from the signal data set, wherein the intermediate residue data set comprises an alpha shape or a Delaunay triangle mesh data object of the signal data set; and
        generating, by the processor, one or more geometric features and/or the dynamical properties of the alpha shape or the Delaunay triangle mesh, wherein the geometric features and/or the dynamical properties include at least one of:
            a 3D volume value,
            a void value,
            a surface area value,
            a principal curvature direction value and
            a Betti number value,
        of the alpha shape or the Delaunay triangle mesh,
    wherein the generated one or more geometric features and/or dynamical properties of the alpha shape or the Delaunay triangle mesh are used as variables representative of the subject in a machine learning operation to detect the one or more cardiac pathologies of the subject.

14. The method of claim 13, wherein the wherein the intermediate residue data set is generated by:
    generating, by the processor, a model of the signal data set;
    determining, by the processor, a residue data object between the model and the signal data set, wherein the alpha shape or a Delaunay triangle mesh data object is generated from the residue data object of the signal data set.

15. The method of claim 13, wherein the signal data set includes cardiac data acquired via at least one channel, each of a biopotential signal acquired over a plurality of heart beats as the long cardiac gradient record.

16. The method of claim 15, wherein the electrophysiological signal data set are acquired for at least 210 seconds, and wherein a portion of the long cardiac gradient record are modeled to generate the residue data object.

17. The method of claim 13, wherein the signal data set comprises a plurality of wide-band gradient signals simultaneously captured via a plurality of channels, including the at least one channel, and wherein a temporal lag or skew between each of the channels is less than about 10 femtoseconds.

18. The method of claim 17, wherein each of the plurality of wide-band gradient signals is unfiltered prior to, and during, the transformation operation, to generate the signal data set.

19. The method of claim 17, wherein each of the plurality of wide-band gradient signals comprises cardiac data that in a frequency domain have frequency components greater than about 1 kHz.

20. The method of claim 17, wherein each of the plurality of wide-band gradient signals comprises cardiac data that in a frequency domain have frequency components of at least 8 kHz.

21. A system for detecting one or more pathologies of a human subject, comprising:
an analysis system configured with computer readable instructions to retrieve an electrophysiological signal data set that (i) is associated with the subject and (ii) has been acquired by measuring equipment configured to non-invasively capture, via one or more sensors, the signal data set as a long cardiac gradient record that exhibits complex non-linear variability, the analysis system using the signal data set to detect the one or more pathologies of the subject,
wherein the detection operation comprises:
generating, by a processor executing a transformation operation, an intermediate residue data set from the signal data set, wherein the intermediate residue data set comprises an alpha shape or a Delaunay triangle mesh data object of the signal data set;
generating, by the processor, one or more geometric features and/or dynamical properties of the alpha shape or the Delaunay triangle mesh, wherein the geometric features and/or the dynamical properties include at least one of:
a 3D volume value,
a void value,
a surface area value,
a principal curvature direction value, and
a Betti number value,
of the alpha shape or the Delaunay triangle mesh,
determining, by the processor, presence or non-presence of abnormal arterial characteristics, wherein the determination comprises an application of the generated one or more geometric features and/or dynamical properties of the alpha shape or the Delaunay triangle mesh in a machine learning operation; and
storing, by the processor, in a computer readable medium, an indication of the determined presence or non-presence of ischemic myocardium, wherein the indication is subsequently retrieved and used to diagnose the one or more pathologies of the subject.

22. The system of claim 21, wherein the intermediate residue data set is generated by:
generating, by the processor, a model of the signal data set;
determining, by the processor, a residue data object between the model and the signal data set, wherein the alpha shape or a Delaunay triangle mesh data object is generated from the residue data object of the signal data set.

23. The system of claim 21, wherein the signal data set includes cardiac data acquired via two or more channels, each of a biopotential signal acquired over a plurality of heart beats as the long cardiac gradient record.

24. The system of claim 23, wherein the signal data set is acquired for at least 210 seconds, and wherein a portion of the long cardiac gradient record is modeled to generate the residue data object.

25. The system of claim 21, wherein the signal data set comprises a plurality of wide-band gradient signals simultaneously captured via a plurality of channels, including the two or more channels, and wherein a temporal lag or skew between each of the channels is less than about 10 femtoseconds.

26. The system of claim 25, wherein each of the plurality of wide-band gradient signals is unfiltered prior to, and during, the transformation operation, to generate the signal data set.

27. The system of claim 25, wherein each of the plurality of wide-band gradient signals comprises cardiac data that in a frequency domain have frequency components greater than about 1 kHz.

28. The system of claim 25, wherein each of the plurality of wide-band gradient signals
comprises cardiac data that in a frequency domain have frequency components of at least 8 kHz.

29. The system of claim 21, wherein the one or more sensors comprise at least one of a surface electrode, an intracardiac electrode, and a non-contact electrode.

30. The system of claim 21, wherein the machine learning operation comprises an artificial neural network algorithm or a regression random forest algorithm.

31. The system of claim 21, wherein the measuring equipment is configured to transmit the signal data set over a network to the analysis system.

32. The system of claim 31, further comprising:
a storage area network, wherein the measuring equipment is configured to transmit the signal data set over the network to the storage area network, and wherein the analysis system is configured to retrieve the acquired signal data set from the storage area network for analysis.

33. A method comprising:
retrieving, by a processor, from a storage area network, an electrophysiological signal data set that (i) is associated with a human subject and (ii) has been acquired by measuring equipment configured to non-invasively capture, via one or more sensors, the signal data set as a long cardiac gradient record that exhibits complex non-linear variability; and
detecting one or more cardiac pathologies of the subject using the signal data set, wherein the detection operation comprises:
generating, by the processor executing a transformation operation, an intermediate residue data set from the signal data set, wherein the intermediate residue data set comprises an alpha shape or a Delaunay triangle mesh data object of the signal data set;
generating, by the processor, one or more geometric features and/or the dynamical properties of the alpha shape or the Delaunay triangle mesh, wherein the geometric features and/or the dynamical properties include at least one of:
- a 3D volume value,
- a void value,
- a surface area value,
- a principal curvature direction value and
- a Betti number value, of the alpha shape or the Delaunay triangle mesh, determining, by the processor, presence or non-presence of abnormal arterial characteristics, wherein the determination comprises an application of the generated one or more geometric features and/or dynamical properties of the alpha shape or the Delaunay triangle mesh in a machine learning operation; and storing, by the processor, in a computer readable medium, an indication of the determined presence or non-presence of ischemic myocardium, wherein the indication is subsequently retrieved and used to diagnose the one or more pathologies of the subject.

34. The method of claim 33, wherein the wherein the intermediate residue data set is generated by:

generating, by the processor, a model of the signal data set;

determining, by the processor, a residue data object between the model and the signal data set, wherein the alpha shape or a Delaunay triangle mesh data object is generated from the residue data object of the signal data set.

35. The method of claim 33, wherein the signal data set includes cardiac data acquired via at least one channel, each of a biopotential signal acquired over a plurality of heart beats as the long cardiac gradient record.

36. The method of claim 35, wherein the electrophysiological signal data set are acquired for at least 210 seconds, and wherein a portion of the long cardiac gradient record are modeled to generate the residue data object.

37. The method of claim 33, wherein the signal data set comprises a plurality of wide-band gradient signals simultaneously captured via a plurality of channels, including the at least one channel, and wherein a temporal lag or skew between each of the channels is less than about 10 femtoseconds.

38. The method of claim 37, wherein each of the plurality of wide-band gradient signals is unfiltered prior to, and during, the transformation operation, to generate the signal data set.

39. The method of claim 37, wherein each of the plurality of wide-band gradient signals comprises cardiac data that in a frequency domain have frequency components greater than about 1 kHz.

40. The method of claim 37, wherein each of the plurality of wide-band gradient signals comprises cardiac data that in a frequency domain have frequency components of at least 8 kHz.

* * * * *